United States Patent
Shemwell et al.

(10) Patent No.: US 9,474,561 B2
(45) Date of Patent: Oct. 25, 2016

(54) TWO-WIRE TECHNIQUE FOR INSTALLING HAMMERTOE IMPLANT

(71) Applicant: Wright Medical Technology, Inc., Arlington, TN (US)

(72) Inventors: Jessica Lauren Shemwell, Drummonds, TN (US); Daniel Francis McCormick, Memphis, TN (US)

(73) Assignee: Wright Medical Technology, Inc., Memphis, TN (US)

( * ) Notice: Subject to any disclaimer, the term of this patent is extended or adjusted under 35 U.S.C. 154(b) by 257 days.

(21) Appl. No.: 14/083,631

(22) Filed: Nov. 19, 2013

(65) Prior Publication Data

US 2015/0142066 A1    May 21, 2015

(51) Int. Cl.
*A61B 17/72* (2006.01)
*A61B 17/88* (2006.01)
*A61B 17/56* (2006.01)

(52) U.S. Cl.
CPC ....... *A61B 17/8888* (2013.01); *A61B 17/7291* (2013.01); *A61B 17/8883* (2013.01); *A61B 2017/564* (2013.01)

(58) Field of Classification Search
CPC .............. A61B 17/72; A61B 17/7208; A61B 17/7216; A61B 17/7225; A61B 17/7233; A61B 17/7283; A61B 17/7291; A61B 17/88; A61B 17/8875; A61B 17/8877; A61B 17/8883; A61B 17/8886; A61B 17/8891; A61B 17/8897; A61B 2017/564
See application file for complete search history.

(56) References Cited

U.S. PATENT DOCUMENTS

| 321,389 A | 6/1885 | Schirmer |
| 346,148 A | 7/1886 | Durham |
| 348,589 A | 9/1886 | Sloan |
| 373,074 A | 11/1887 | Jones |
| 430,236 A | 6/1890 | Rogers |
| 561,968 A | 6/1896 | Coulon |

(Continued)

FOREIGN PATENT DOCUMENTS

| CN | 201085677 | 7/2008 |
| EP | 0127994 | 12/1984 |

(Continued)

OTHER PUBLICATIONS

U.S. Appl. No. 13/086,136—Non-Final Office Action dated Feb. 4, 2013, 6 pages.

(Continued)

*Primary Examiner* — Christian Sevilla
*Assistant Examiner* — Eric S Gibson
(74) *Attorney, Agent, or Firm* — Duane Morris LLP

(57) ABSTRACT

A method includes inserting a first surgical device into an exposed first end of a first bone until a trailing end of the first surgical device is disposed adjacent to the first end of the first bone. A second surgical device is inserted into an exposed first end of a second bone while the first surgical device remains disposed within the first bone. A first portion of an implant is advanced into the second bone while being engaged with a passageway defined by the implant such that the implant is guided by the second surgical device. The second surgical device is removed from the second bone and from its engagement with the implant. The first bone is repositioned such that the first surgical device is aligned with the passageway defined by the implant, and the first bone is forced into engagement with a second portion of the implant.

16 Claims, 39 Drawing Sheets

(56) References Cited

U.S. PATENT DOCUMENTS

| | | | |
|---|---|---|---|
| 736,121 A | 8/1903 | Lipscomb |
| 821,025 A | 5/1906 | Davies |
| 882,937 A | 3/1908 | Pegley |
| 1,966,835 A | 7/1934 | Stites |
| 2,140,749 A | 12/1938 | Kaplan |
| 2,361,107 A | 10/1944 | Johnson |
| 2,451,747 A | 10/1948 | Kindt |
| 2,490,364 A | 12/1949 | Livingston |
| 2,600,517 A | 6/1952 | Rushing |
| 2,697,370 A | 12/1954 | Brooks |
| 2,832,245 A | 4/1958 | Burrows |
| 2,895,368 A | 7/1959 | Place |
| 3,462,765 A | 8/1969 | Swanson |
| 3,466,669 A * | 9/1969 | Flatt | A61F 2/4241 623/21.17 |
| 3,593,342 A | 7/1971 | Niebauer et al. |
| 3,681,786 A | 8/1972 | Lynch |
| 3,739,403 A | 6/1973 | Nicolle |
| 3,759,257 A | 9/1973 | Fischer et al. |
| 3,760,802 A | 9/1973 | Fischer et al. |
| 3,779,239 A | 12/1973 | Fischer et al. |
| 3,824,631 A | 7/1974 | Burstein et al. |
| D243,716 S | 3/1977 | Treace et al. |
| 4,047,524 A | 9/1977 | Hall |
| 4,096,896 A | 6/1978 | Engel |
| 4,156,296 A | 5/1979 | Johnson et al. |
| 4,170,990 A | 10/1979 | Baumgart et al. |
| 4,175,555 A | 11/1979 | Herbert |
| 4,198,713 A | 4/1980 | Swanson |
| 4,204,284 A | 5/1980 | Koeneman |
| 4,213,208 A | 7/1980 | Marne |
| 4,237,875 A | 12/1980 | Termanini |
| 4,262,665 A | 4/1981 | Roalstad et al. |
| 4,263,903 A | 4/1981 | Griggs |
| 4,275,717 A | 6/1981 | Bolesky |
| 4,276,660 A | 7/1981 | Laure |
| 4,278,091 A | 7/1981 | Borzone |
| 4,304,011 A | 12/1981 | Whelan, III |
| 4,321,002 A | 3/1982 | Froehlich |
| 4,364,382 A | 12/1982 | Mennen |
| 4,367,562 A | 1/1983 | Gauthier |
| 4,404,874 A | 9/1983 | Lieser |
| 4,434,796 A | 3/1984 | Karapetian et al. |
| 4,454,875 A | 6/1984 | Pratt et al. |
| 4,485,816 A | 12/1984 | Krumme |
| D277,509 S | 2/1985 | Lawrence et al. |
| D277,784 S | 2/1985 | Sgariato et al. |
| 4,516,569 A | 5/1985 | Evans et al. |
| 4,570,623 A | 2/1986 | Ellison et al. |
| 4,590,928 A | 5/1986 | Hunt et al. |
| D284,099 S | 6/1986 | Laporta et al. |
| 4,634,382 A | 1/1987 | Kusano et al. |
| 4,642,122 A | 2/1987 | Steffee |
| 4,655,661 A | 4/1987 | Brandt |
| D291,731 S | 9/1987 | Alkins |
| 4,723,540 A | 2/1988 | Gilmer, Jr. |
| 4,723,541 A | 2/1988 | Reese |
| 4,731,087 A | 3/1988 | Sculco et al. |
| 4,756,711 A | 7/1988 | Mai et al. |
| 4,759,768 A | 7/1988 | Hermann et al. |
| 4,790,304 A | 12/1988 | Rosenberg |
| 4,865,606 A | 9/1989 | Rehder |
| 4,908,031 A | 3/1990 | Frisch |
| 4,915,092 A | 4/1990 | Firica et al. |
| 4,932,974 A | 6/1990 | Pappas et al. |
| 4,940,467 A | 7/1990 | Tronzo |
| 4,955,916 A | 9/1990 | Carignan et al. |
| 4,963,144 A | 10/1990 | Huene |
| 4,969,909 A * | 11/1990 | Barouk | A61B 17/72 606/62 |
| 5,002,563 A | 3/1991 | Pyka et al. |
| 5,007,932 A | 4/1991 | Bekki et al. |
| 5,011,497 A * | 4/1991 | Persson | A61F 2/4241 623/21.15 |
| 5,019,079 A | 5/1991 | Ross |
| 5,029,753 A | 7/1991 | Hipon et al. |
| 5,037,440 A | 8/1991 | Koenig |
| 5,046,513 A | 9/1991 | Gatturna et al. |
| 5,047,059 A | 9/1991 | Saffar |
| 5,053,038 A | 10/1991 | Sheehan |
| 5,059,193 A | 10/1991 | Kuslich |
| 5,062,851 A | 11/1991 | Branemark |
| 5,089,009 A | 2/1992 | Green |
| 5,092,896 A | 3/1992 | Meuli et al. |
| 5,108,395 A | 4/1992 | Laurain |
| 5,133,761 A | 7/1992 | Krouskop |
| 5,147,363 A | 9/1992 | Harle |
| 5,171,252 A | 12/1992 | Friedland |
| 5,179,915 A | 1/1993 | Cohen et al. |
| 5,190,546 A | 3/1993 | Jervis |
| 5,199,839 A | 4/1993 | DeHaitre |
| 5,207,712 A | 5/1993 | Cohen |
| 5,209,756 A | 5/1993 | Seedhom et al. |
| 5,213,347 A | 5/1993 | Rulon et al. |
| 5,222,975 A | 6/1993 | Crainich |
| 5,246,443 A | 9/1993 | Mai |
| 5,281,225 A | 1/1994 | Vicenzi |
| 5,304,204 A | 4/1994 | Bregen |
| 5,324,307 A | 6/1994 | Jarrett et al. |
| 5,326,364 A | 7/1994 | Clift, Jr. et al. |
| 5,326,366 A | 7/1994 | Pascarella et al. |
| 5,330,476 A | 7/1994 | Hiot et al. |
| 5,342,396 A | 8/1994 | Cook |
| 5,352,229 A | 10/1994 | Goble et al. |
| 5,354,301 A | 10/1994 | Castellano |
| 5,358,405 A | 10/1994 | Imai |
| 5,360,450 A | 11/1994 | Giannini |
| 5,366,479 A | 11/1994 | McGarry et al. |
| 5,380,334 A | 1/1995 | Torrie et al. |
| 5,395,372 A | 3/1995 | Holt et al. |
| 5,405,400 A | 4/1995 | Linscheid et al. |
| 5,405,401 A | 4/1995 | Lippincott, III et al. |
| 5,417,692 A | 5/1995 | Goble et al. |
| 5,425,776 A | 6/1995 | Cohen |
| 5,425,777 A | 6/1995 | Sarkisian et al. |
| 5,437,674 A | 8/1995 | Worcel et al. |
| 5,449,359 A | 9/1995 | Groiso |
| 5,454,814 A | 10/1995 | Comte |
| 5,458,648 A | 10/1995 | Berman et al. |
| 5,470,230 A | 11/1995 | Daftary et al. |
| 5,474,557 A | 12/1995 | Mai |
| 5,480,447 A * | 1/1996 | Skiba | A61F 2/4225 623/21.19 |
| 5,484,443 A | 1/1996 | Pascarella et al. |
| 5,498,265 A | 3/1996 | Asnis et al. |
| 5,507,822 A | 4/1996 | Bouchon et al. |
| 5,516,248 A | 5/1996 | DeHaitre |
| 5,522,903 A | 6/1996 | Sokolow et al. |
| 5,529,075 A | 6/1996 | Clark |
| 5,536,127 A | 7/1996 | Pennig |
| 5,549,681 A | 8/1996 | Segmüller et al. |
| 5,551,871 A | 9/1996 | Besselink et al. |
| 5,554,157 A | 9/1996 | Errico et al. |
| 5,578,034 A | 11/1996 | Estes |
| 5,591,165 A | 1/1997 | Jackson |
| 5,595,563 A | 1/1997 | Moisdon |
| 5,601,558 A | 2/1997 | Torrie et al. |
| D378,409 S | 3/1997 | Michelson |
| 5,634,925 A | 6/1997 | Urbanski |
| 5,643,264 A | 7/1997 | Sherman et al. |
| 5,645,599 A | 7/1997 | Samani |
| 5,660,188 A | 8/1997 | Groiso |
| 5,669,913 A | 9/1997 | Zobel |
| 5,674,297 A | 10/1997 | Lane et al. |
| 5,683,466 A * | 11/1997 | Vitale | A61F 2/30756 623/21.15 |
| 5,690,629 A | 11/1997 | Asher et al. |
| 5,702,472 A | 12/1997 | Huebner |
| 5,707,395 A | 1/1998 | Li |
| 5,713,903 A | 2/1998 | Sander et al. |
| 5,713,904 A | 2/1998 | Errico et al. |
| 5,720,753 A | 2/1998 | Sander et al. |
| 5,725,585 A | 3/1998 | Zobel |
| 5,728,127 A | 3/1998 | Asher et al. |

(56) References Cited

U.S. PATENT DOCUMENTS

| | | |
|---|---|---|
| 5,733,307 A | 3/1998 | Dinsdale |
| 5,741,256 A | 4/1998 | Bresina |
| 5,749,916 A | 5/1998 | Richelsoph |
| 5,769,852 A | 6/1998 | Brångnemark |
| 5,776,202 A | 7/1998 | Copf et al. |
| 5,779,707 A | 7/1998 | Berthelet et al. |
| 5,782,927 A | 7/1998 | Klawitter et al. |
| 5,785,713 A | 7/1998 | Jobe |
| 5,840,078 A | 11/1998 | Yerys |
| 5,853,414 A | 12/1998 | Groiso |
| 5,876,434 A | 3/1999 | Flomenblit et al. |
| 5,882,444 A | 3/1999 | Flomenblit et al. |
| 5,893,850 A | 4/1999 | Cachia |
| 5,919,193 A | 7/1999 | Slavitt |
| 5,928,236 A | 7/1999 | Augagneur et al. |
| 5,941,890 A | 8/1999 | Voegele et al. |
| 5,951,288 A | 9/1999 | Sawa |
| 5,958,159 A | 9/1999 | Prandi |
| 5,980,524 A | 11/1999 | Justin et al. |
| 5,984,970 A | 11/1999 | Bramlet |
| 5,984,971 A | 11/1999 | Faccioli et al. |
| 6,011,497 A | 1/2000 | Tsang et al. |
| 6,017,366 A | 1/2000 | Berman |
| 6,030,162 A | 2/2000 | Huebner |
| 6,045,573 A | 4/2000 | Wenstrom et al. |
| 6,048,151 A | 4/2000 | Kwee |
| 6,048,343 A | 4/2000 | Mathis et al. |
| 6,083,242 A | 7/2000 | Cook |
| 6,099,571 A | 8/2000 | Knapp |
| 6,102,642 A | 8/2000 | Kawashita et al. |
| 6,146,387 A | 11/2000 | Trott et al. |
| 6,187,009 B1 | 2/2001 | Herzog et al. |
| 6,193,757 B1 | 2/2001 | Foley et al. |
| 6,197,037 B1 | 3/2001 | Hair |
| 6,200,321 B1 | 3/2001 | Orbay et al. |
| 6,200,330 B1 | 3/2001 | Benderev et al. |
| 6,200,345 B1 | 3/2001 | Morgan |
| 6,224,600 B1 | 5/2001 | Protogirou |
| 6,248,109 B1 | 6/2001 | Stofella |
| 6,299,613 B1 | 10/2001 | Ogilvie et al. |
| 6,305,053 B1 | 10/2001 | Galbreath |
| 6,306,140 B1 | 10/2001 | Siddiqui |
| 6,319,284 B1 | 11/2001 | Rushdy et al. |
| 6,332,885 B1 | 12/2001 | Martella |
| 6,336,928 B1 | 1/2002 | Guerin et al. |
| 6,352,560 B1 | 3/2002 | Poeschmann et al. |
| 6,383,223 B1 | 5/2002 | Baehler et al. |
| 6,386,877 B1 | 5/2002 | Sutter |
| 6,406,234 B2 | 6/2002 | Frigg |
| 6,413,260 B1 | 7/2002 | Berrevoets et al. |
| 6,419,706 B1 | 7/2002 | Graf |
| 6,423,097 B2 | 7/2002 | Rauscher |
| 6,428,634 B1 | 8/2002 | Besselink et al. |
| 6,436,099 B1 | 8/2002 | Drewry et al. |
| 6,451,057 B1 | 9/2002 | Chen et al. |
| 6,454,808 B1 | 9/2002 | Masada |
| 6,458,134 B1 | 10/2002 | Songer et al. |
| 6,475,242 B1 | 11/2002 | Bramlet |
| 6,508,841 B2 | 1/2003 | Martin et al. |
| 6,517,543 B1 | 2/2003 | Berrevoets et al. |
| 6,533,788 B1 | 3/2003 | Orbay |
| 6,551,321 B1 | 4/2003 | Burkinshaw |
| 6,551,343 B1 | 4/2003 | Törmälä et al. |
| 6,575,973 B1 | 6/2003 | Shekalim |
| 6,575,976 B2 | 6/2003 | Grafton |
| 6,582,453 B1 | 6/2003 | Tran et al. |
| 6,648,890 B2 | 11/2003 | Culbert et al. |
| 6,679,668 B2 | 1/2004 | Martin et al. |
| 6,682,565 B1 | 1/2004 | Krishnan |
| 6,685,706 B2 | 2/2004 | Padget et al. |
| 6,699,247 B2 | 3/2004 | Zucherman et al. |
| 6,699,292 B2 | 3/2004 | Ogilvie et al. |
| 6,706,045 B2 | 3/2004 | Lin et al. |
| 6,767,350 B1 | 7/2004 | Lob |
| 6,773,437 B2 | 8/2004 | Ogilvie et al. |
| 6,811,568 B2 | 11/2004 | Minamikawa |
| 6,869,449 B2 | 3/2005 | Ball et al. |
| 6,875,235 B2 | 4/2005 | Ferree |
| 7,037,309 B2* | 5/2006 | Weil .............. A61B 17/863 606/304 |
| 7,037,324 B2 | 5/2006 | Martinek |
| 7,037,342 B2 | 5/2006 | Nilsson et al. |
| 7,041,106 B1* | 5/2006 | Carver ............ A61B 17/7291 606/309 |
| 7,044,953 B2 | 5/2006 | Capanni |
| 7,112,214 B2 | 9/2006 | Peterson et al. |
| 7,182,787 B2 | 2/2007 | Hassler et al. |
| 7,192,445 B2 | 3/2007 | Ellingsen et al. |
| 7,207,994 B2 | 4/2007 | Vlahos et al. |
| 7,240,677 B2 | 7/2007 | Fox |
| 7,261,716 B2 | 8/2007 | Strobel |
| 7,291,175 B1 | 11/2007 | Gordon |
| 7,569,061 B2 | 8/2009 | Colleran |
| 7,585,316 B2 | 9/2009 | Trieu |
| 7,588,603 B2 | 9/2009 | Leonard |
| 7,695,471 B2 | 4/2010 | Cheung et al. |
| 7,708,759 B2 | 5/2010 | Lubbers et al. |
| 7,727,235 B2 | 6/2010 | Contiliano et al. |
| 7,780,701 B1 | 8/2010 | Meridew et al. |
| 7,780,737 B2 | 8/2010 | Bonnard et al. |
| 7,785,357 B2 | 8/2010 | Guan et al. |
| 7,837,738 B2 | 11/2010 | Reigstad et al. |
| 7,842,091 B2 | 11/2010 | Johnstone et al. |
| 7,887,589 B2 | 2/2011 | Glenn et al. |
| 7,909,880 B1 | 3/2011 | Grant |
| 7,918,879 B2 | 4/2011 | Yeung et al. |
| 7,959,681 B2 | 6/2011 | Lavi |
| 7,963,995 B2 | 6/2011 | Richelsoph |
| 7,976,565 B1 | 7/2011 | Meridew |
| 7,985,246 B2 | 7/2011 | Trieu |
| 8,002,811 B2 | 8/2011 | Corradi et al. |
| 8,057,524 B2 | 11/2011 | Meridew |
| 8,100,983 B2 | 1/2012 | Schulte |
| 8,118,839 B2 | 2/2012 | Taylor |
| 8,118,849 B2 | 2/2012 | Wahl et al. |
| 8,197,509 B2 | 6/2012 | Contiliano et al. |
| 8,262,712 B2 | 9/2012 | Coilard-Lavirotte et al. |
| 8,267,939 B2 | 9/2012 | Cipoletti et al. |
| 8,337,537 B2 | 12/2012 | Pelo et al. |
| 8,394,097 B2 | 3/2013 | Peyrot et al. |
| 8,394,132 B2 | 3/2013 | Lewis et al. |
| 8,414,583 B2 | 4/2013 | Prandi et al. |
| 8,465,525 B2 | 6/2013 | Hawkins et al. |
| 8,475,456 B2 | 7/2013 | Augoyard et al. |
| 8,523,944 B2 | 9/2013 | Jimenez et al. |
| 8,591,545 B2 | 11/2013 | Lunn et al. |
| 8,608,785 B2 | 12/2013 | Reed et al. |
| 8,616,091 B2 | 12/2013 | Anderson |
| 8,636,457 B2 | 1/2014 | Connors |
| 8,641,769 B2 | 2/2014 | Malandain |
| 8,647,390 B2 | 2/2014 | Bellemere et al. |
| 8,764,842 B2 | 7/2014 | Graham |
| 8,840,677 B2 | 9/2014 | Kale et al. |
| 8,888,779 B2 | 11/2014 | Senn |
| D720,072 S | 12/2014 | Cheney et al. |
| 8,906,060 B2 | 12/2014 | Hart |
| 8,986,386 B2 | 3/2015 | Oglaza et al. |
| 8,998,999 B2 | 4/2015 | Lewis et al. |
| 9,044,287 B2 | 6/2015 | Reed et al. |
| 9,056,014 B2 | 6/2015 | McCormick et al. |
| 9,125,704 B2 | 9/2015 | Reed et al. |
| 9,138,274 B1* | 9/2015 | Biesinger .......... A61B 17/7225 |
| 9,149,268 B2 | 10/2015 | Graul et al. |
| 2001/0025199 A1 | 9/2001 | Rauscher |
| 2001/0028836 A1 | 10/2001 | Kohori |
| 2001/0049529 A1 | 12/2001 | Cachia et al. |
| 2002/0019636 A1 | 2/2002 | Ogilvie et al. |
| 2002/0022887 A1 | 2/2002 | Huene |
| 2002/0026194 A1 | 2/2002 | Morrison et al. |
| 2002/0055785 A1 | 5/2002 | Harris |
| 2002/0065561 A1 | 5/2002 | Ogilvie et al. |
| 2002/0068939 A1 | 6/2002 | Levy et al. |
| 2002/0072803 A1 | 6/2002 | Saunders et al. |
| 2002/0082705 A1 | 6/2002 | Bouman et al. |

(56) References Cited

U.S. PATENT DOCUMENTS

| | | |
|---|---|---|
| 2002/0111690 A1 | 8/2002 | Hyde |
| 2002/0128713 A1 | 9/2002 | Ferree |
| 2002/0165544 A1 | 11/2002 | Perren et al. |
| 2002/0183846 A1 | 12/2002 | Kuslich et al. |
| 2003/0032961 A1 | 2/2003 | Pelo et al. |
| 2003/0040805 A1 | 2/2003 | Minamikawa |
| 2003/0069645 A1 | 4/2003 | Ball et al. |
| 2003/0130660 A1 | 7/2003 | Levy et al. |
| 2003/0191422 A1 | 10/2003 | Sossong |
| 2003/0233095 A1 | 12/2003 | Urbanski et al. |
| 2004/0010315 A1 | 1/2004 | Song |
| 2004/0093081 A1 | 5/2004 | Nilsson et al. |
| 2004/0097941 A1 | 5/2004 | Weiner et al. |
| 2004/0102853 A1 | 5/2004 | Boumann et al. |
| 2004/0111117 A1 | 6/2004 | Colleran et al. |
| 2004/0133204 A1 | 7/2004 | Davies |
| 2004/0138756 A1 | 7/2004 | Reeder |
| 2004/0220574 A1 | 11/2004 | Pelo et al. |
| 2004/0220678 A1 | 11/2004 | Chow et al. |
| 2004/0230193 A1 | 11/2004 | Cheung et al. |
| 2004/0230194 A1 | 11/2004 | Urbanski et al. |
| 2004/0230313 A1 | 11/2004 | Saunders |
| 2004/0249461 A1 | 12/2004 | Ferree |
| 2005/0113836 A1 | 5/2005 | Lozier et al. |
| 2005/0119757 A1 | 6/2005 | Hassler et al. |
| 2005/0123672 A1 | 6/2005 | Justin et al. |
| 2005/0124443 A1 | 6/2005 | Summers |
| 2005/0149031 A1 | 7/2005 | Ciccone et al. |
| 2005/0177158 A1 | 8/2005 | Doubler et al. |
| 2005/0187636 A1 | 8/2005 | Graham |
| 2005/0251265 A1 | 11/2005 | Calandruccio et al. |
| 2005/0261768 A1 | 11/2005 | Trieu |
| 2005/0283159 A1 | 12/2005 | Amara |
| 2006/0052725 A1 | 3/2006 | Santilli |
| 2006/0052878 A1 | 3/2006 | Schmieding |
| 2006/0074421 A1 | 4/2006 | Bickley et al. |
| 2006/0074488 A1 | 4/2006 | Abdou |
| 2006/0074492 A1 | 4/2006 | Frey |
| 2006/0084998 A1 | 4/2006 | Levy et al. |
| 2006/0100715 A1 | 5/2006 | De Villiers |
| 2006/0129153 A1* | 6/2006 | Klaue ............... A61B 17/68 606/916 |
| 2006/0149258 A1 | 7/2006 | Sousa |
| 2006/0173462 A1 | 8/2006 | Kay et al. |
| 2006/0200151 A1 | 9/2006 | Ducharme et al. |
| 2006/0229617 A1 | 10/2006 | Meller et al. |
| 2006/0247787 A1 | 11/2006 | Rydell et al. |
| 2007/0038303 A1 | 2/2007 | Myerson et al. |
| 2007/0078518 A1 | 4/2007 | Lavi |
| 2007/0106283 A1 | 5/2007 | Garcia et al. |
| 2007/0123873 A1 | 5/2007 | Czartoski et al. |
| 2007/0123993 A1 | 5/2007 | Hassler et al. |
| 2007/0142920 A1 | 6/2007 | Niemi |
| 2007/0177959 A1 | 8/2007 | Chopp et al. |
| 2007/0185583 A1 | 8/2007 | Branemark |
| 2007/0185584 A1 | 8/2007 | Kaufmann et al. |
| 2007/0198018 A1 | 8/2007 | Biedermann et al. |
| 2007/0213831 A1 | 9/2007 | de Cubber |
| 2007/0239158 A1 | 10/2007 | Trieu et al. |
| 2007/0293866 A1 | 12/2007 | Stroeckel et al. |
| 2008/0039949 A1 | 2/2008 | Meesenburg et al. |
| 2008/0051912 A1 | 2/2008 | Hollawell |
| 2008/0086139 A1* | 4/2008 | Bourke ............... A61B 17/68 606/270 |
| 2008/0132894 A1 | 6/2008 | Coilard-Lavirotte et al. |
| 2008/0132958 A1 | 6/2008 | Pech et al. |
| 2008/0154385 A1 | 6/2008 | Trail et al. |
| 2008/0161919 A1 | 7/2008 | Melkent |
| 2008/0177262 A1 | 7/2008 | Augoyard et al. |
| 2008/0177291 A1 | 7/2008 | Jensen et al. |
| 2008/0177334 A1 | 7/2008 | Stinnette |
| 2008/0195215 A1 | 8/2008 | Morton |
| 2008/0195219 A1 | 8/2008 | Wiley et al. |
| 2008/0221574 A1* | 9/2008 | Cavallazzi ......... A61B 17/1739 606/62 |
| 2008/0221697 A1 | 9/2008 | Graser |
| 2008/0221698 A1 | 9/2008 | Berger |
| 2008/0255618 A1 | 10/2008 | Fisher et al. |
| 2008/0269908 A1 | 10/2008 | Warburton |
| 2008/0294204 A1 | 11/2008 | Chirico et al. |
| 2009/0005782 A1 | 1/2009 | Chirico et al. |
| 2009/0012564 A1 | 1/2009 | Chirico et al. |
| 2009/0036893 A1 | 2/2009 | Kartalian et al. |
| 2009/0149891 A1 | 6/2009 | Lee et al. |
| 2009/0163918 A1 | 6/2009 | Levy et al. |
| 2009/0187219 A1 | 7/2009 | Pachtman et al. |
| 2009/0204158 A1 | 8/2009 | Sweeney |
| 2009/0210016 A1 | 8/2009 | Champagne et al. |
| 2009/0216282 A1 | 8/2009 | Blake et al. |
| 2009/0254189 A1 | 10/2009 | Scheker |
| 2009/0254190 A1 | 10/2009 | Gannoe et al. |
| 2009/0259316 A1 | 10/2009 | Ginn et al. |
| 2010/0010637 A1 | 1/2010 | Pequignot |
| 2010/0016982 A1 | 1/2010 | Solomons |
| 2010/0023012 A1 | 1/2010 | Voor |
| 2010/0030221 A1 | 2/2010 | Christian et al. |
| 2010/0049244 A1 | 2/2010 | Cohen et al. |
| 2010/0057214 A1 | 3/2010 | Graham et al. |
| 2010/0061825 A1* | 3/2010 | Liu ............... B25B 13/08 411/388 |
| 2010/0069913 A1 | 3/2010 | Chirico |
| 2010/0069970 A1 | 3/2010 | Lewis et al. |
| 2010/0121390 A1 | 5/2010 | Kleinman |
| 2010/0125274 A1 | 5/2010 | Greenhalgh et al. |
| 2010/0131014 A1 | 5/2010 | Peyrot et al. |
| 2010/0131072 A1* | 5/2010 | Schulte ............... A61B 17/68 623/21.11 |
| 2010/0161068 A1 | 6/2010 | Lindner et al. |
| 2010/0185295 A1 | 7/2010 | Emmanuel |
| 2010/0217325 A1 | 8/2010 | Hochschuler et al. |
| 2010/0249942 A1 | 9/2010 | Goswami et al. |
| 2010/0256639 A1* | 10/2010 | Tyber ............... A61B 17/1717 606/62 |
| 2010/0256770 A1 | 10/2010 | Hakansson et al. |
| 2010/0262254 A1 | 10/2010 | Lawrence et al. |
| 2010/0274293 A1 | 10/2010 | Terrill et al. |
| 2010/0286692 A1 | 11/2010 | Greenhalgh et al. |
| 2010/0292799 A1 | 11/2010 | Hansell et al. |
| 2010/0324556 A1* | 12/2010 | Tyber ............... A61B 17/1717 606/62 |
| 2010/0331893 A1 | 12/2010 | Geist et al. |
| 2011/0004255 A1* | 1/2011 | Weiner ............... A61B 17/1682 606/301 |
| 2011/0004317 A1 | 1/2011 | Hacking et al. |
| 2011/0066190 A1 | 3/2011 | Schaller et al. |
| 2011/0082507 A1* | 4/2011 | Klaue ............... A61B 17/68 606/329 |
| 2011/0082508 A1* | 4/2011 | Reed ............... A61B 17/7225 606/329 |
| 2011/0093017 A1 | 4/2011 | Prasad et al. |
| 2011/0093075 A1 | 4/2011 | Duplessis et al. |
| 2011/0093085 A1 | 4/2011 | Morton |
| 2011/0118739 A1* | 5/2011 | Tyber ............... A61B 17/1717 606/62 |
| 2011/0144644 A1* | 6/2011 | Prandi ............... A61B 17/68 606/62 |
| 2011/0144766 A1 | 6/2011 | Kale et al. |
| 2011/0208252 A1 | 8/2011 | Erhart |
| 2011/0257652 A1* | 10/2011 | Roman ............... A61B 17/7225 606/62 |
| 2011/0301652 A1* | 12/2011 | Reed ............... A61B 17/7291 606/319 |
| 2011/0301653 A1* | 12/2011 | Reed ............... A61B 17/1604 606/319 |
| 2011/0306975 A1 | 12/2011 | Kaikkonen et al. |
| 2011/0319946 A1 | 12/2011 | Levy et al. |
| 2012/0016428 A1 | 1/2012 | White et al. |
| 2012/0065692 A1 | 3/2012 | Champagne et al. |
| 2012/0065738 A1* | 3/2012 | Schulman ............... A61B 17/68 623/23.44 |
| 2012/0089197 A1* | 4/2012 | Anderson ............ A61B 17/7233 606/310 |
| 2012/0136448 A1 | 5/2012 | Seifert et al. |
| 2012/0209337 A1 | 8/2012 | Weinstein |

(56) References Cited

U.S. PATENT DOCUMENTS

| | | |
|---|---|---|
| 2012/0259419 A1 | 10/2012 | Brown et al. |
| 2012/0271362 A1 | 10/2012 | Martineau et al. |
| 2012/0323241 A1 | 12/2012 | McClellan et al. |
| 2013/0030475 A1 | 1/2013 | Weiner et al. |
| 2013/0053975 A1 | 2/2013 | Reed et al. |
| 2013/0060295 A1 | 3/2013 | Reed et al. |
| 2013/0066383 A1* | 3/2013 | Anderson .......... A61B 17/7233 606/329 |
| 2013/0066435 A1* | 3/2013 | Averous .................... A61F 2/42 623/21.11 |
| 2013/0079776 A1* | 3/2013 | Zwirkoski .............. A61B 17/68 606/62 |
| 2013/0090655 A1 | 4/2013 | Tontz |
| 2013/0096634 A1 | 4/2013 | Suh |
| 2013/0123862 A1* | 5/2013 | Anderson .............. A61B 17/88 606/321 |
| 2013/0131822 A1* | 5/2013 | Lewis .................. A61F 2/4606 623/21.19 |
| 2013/0150965 A1* | 6/2013 | Taylor ...................... A61F 2/30 623/16.11 |
| 2013/0190761 A1 | 7/2013 | Prandi et al. |
| 2013/0211451 A1 | 8/2013 | Wales et al. |
| 2013/0226191 A1* | 8/2013 | Thoren .............. A61B 17/8886 606/104 |
| 2013/0253597 A1 | 9/2013 | Augoyard et al. |
| 2013/0274814 A1 | 10/2013 | Weiner et al. |
| 2013/0317559 A1* | 11/2013 | Leavitt ............... A61B 17/1697 606/86 R |
| 2013/0325138 A1 | 12/2013 | Graham |
| 2014/0018930 A1* | 1/2014 | Oster .................... A61F 2/4261 623/21.12 |
| 2014/0025125 A1 | 1/2014 | Sack et al. |
| 2014/0052196 A1* | 2/2014 | McGinley .......... A61B 17/8605 606/319 |
| 2014/0107713 A1 | 4/2014 | Pech et al. |
| 2014/0135768 A1 | 5/2014 | Roman |
| 2014/0142715 A1* | 5/2014 | McCormick ....... A61B 17/8883 623/21.19 |
| 2014/0180428 A1 | 6/2014 | McCormick |
| 2014/0188179 A1 | 7/2014 | McCormick |
| 2014/0188237 A1 | 7/2014 | McCormick et al. |
| 2014/0188239 A1* | 7/2014 | Cummings ........ A61B 17/7291 623/21.19 |
| 2014/0257289 A1 | 9/2014 | Kecman et al. |
| 2014/0276825 A1 | 9/2014 | Brown et al. |
| 2014/0277185 A1 | 9/2014 | Boileau et al. |
| 2014/0277186 A1 | 9/2014 | Granberry et al. |
| 2015/0012098 A1 | 1/2015 | Eastlack et al. |
| 2015/0018954 A1 | 1/2015 | Loebl et al. |
| 2015/0073413 A1* | 3/2015 | Palmer ............... A61B 17/7266 606/63 |
| 2015/0088136 A1 | 3/2015 | Kotuljac et al. |
| 2015/0088266 A1 | 3/2015 | Sander et al. |
| 2015/0094778 A1 | 4/2015 | McCormick et al. |
| 2015/0112342 A1* | 4/2015 | Penzimer .......... A61B 17/8875 606/63 |
| 2015/0141994 A1 | 5/2015 | Cheney et al. |
| 2015/0142066 A1* | 5/2015 | Shemwell .......... A61B 17/8888 606/301 |
| 2015/0164563 A1 | 6/2015 | Lewis et al. |
| 2015/0223848 A1 | 8/2015 | McCormick et al. |
| 2015/0223849 A1* | 8/2015 | McCormick ....... A61B 17/7291 606/63 |
| 2015/0342655 A1 | 12/2015 | Reed et al. |

FOREIGN PATENT DOCUMENTS

| | | |
|---|---|---|
| EP | 0340159 | 11/1989 |
| EP | 0409364 | 1/1991 |
| EP | 0545830 | 6/1993 |
| EP | 0551846 | 7/1993 |
| EP | 0611557 | 8/1994 |
| EP | 0738502 | 10/1996 |
| EP | 880950 A1 | 12/1998 |
| EP | 1300122 | 4/2003 |
| EP | 1825826 A1 | 8/2007 |
| EP | 1870050 A2 | 12/2007 |
| EP | 1708653 | 9/2009 |
| EP | 1923012 | 6/2010 |
| EP | 1868536 | 11/2010 |
| EP | 2275055 | 5/2012 |
| EP | 2221025 | 12/2012 |
| EP | 2221026 | 3/2013 |
| EP | 2564799 A1 | 3/2013 |
| EP | 2774556 A1 | 9/2014 |
| FR | 736058 | 11/1932 |
| FR | 1036978 | 9/1953 |
| FR | 2603794 | 3/1988 |
| FR | 2605878 | 5/1988 |
| FR | 2628312 | 9/1989 |
| FR | 2645735 | 10/1990 |
| FR | 2651119 | 3/1991 |
| FR | 2663838 A1 | 1/1993 |
| FR | 2694696 | 2/1994 |
| FR | 2725126 | 4/1996 |
| FR | 2743490 | 7/1997 |
| FR | 2754702 | 4/1998 |
| FR | 2783702 | 3/2000 |
| FR | 2787313 | 6/2000 |
| FR | 2794019 | 12/2000 |
| FR | 2801189 A1 | 5/2001 |
| FR | 2846545 | 5/2004 |
| FR | 2728779 A1 | 7/2005 |
| FR | 2884406 | 10/2006 |
| FR | 2927529 A1 | 8/2009 |
| FR | 2935601 A1 | 3/2010 |
| GB | 140983 | 4/1920 |
| GB | 2119655 | 11/1983 |
| GB | 2227540 | 1/1990 |
| GB | 2336415 | 10/1999 |
| GB | 2430625 | 4/2007 |
| JP | S53-128181 A | 11/1978 |
| JP | 60145133 | 7/1985 |
| JP | H07-500520 A | 1/1995 |
| JP | 07303662 | 11/1995 |
| JP | 2004535249 | 11/2004 |
| JP | 2007530194 | 11/2007 |
| JP | 2008-188411 A | 8/2008 |
| JP | 2009-160399 A | 7/2009 |
| JP | 2010-046481 A | 3/2010 |
| JP | 2011-502584 A | 1/2011 |
| JP | 2011-525229 A | 9/2011 |
| SU | 1152582 | 4/1985 |
| WO | WO 92/17122 | 10/1992 |
| WO | WO 96/41596 | 12/1996 |
| WO | WO 98/17189 | 4/1998 |
| WO | WO 98/47449 | 10/1998 |
| WO | WO 99/21515 A1 | 5/1999 |
| WO | WO 01/80751 A1 | 11/2001 |
| WO | WO 02/34107 | 5/2002 |
| WO | WO 2005/063149 | 7/2005 |
| WO | WO2005094706 | 10/2005 |
| WO | WO 2005/104961 | 11/2005 |
| WO | WO 2006/103598 | 10/2006 |
| WO | WO2006109004 | 10/2006 |
| WO | WO2007135322 | 11/2007 |
| WO | WO 2009/155577 | 12/2009 |
| WO | WO 2013/096746 | 6/2013 |
| WO | WO 2013/131974 A1 | 9/2013 |
| WO | WO 2014/165123 | 10/2014 |

OTHER PUBLICATIONS

U.S. Appl. No. 13/086,136—Final Office Action dated Sep. 18, 2013, 9 pages.

U.S. Appl. No. 13/086,136—Non-Final Office Action dated Dec. 30, 2013, 11 pages.

U.S. Appl. No. 13/086,136—Final Office Action dated May 29, 2014, 14 pages.

U.S. Appl. No. 13/086,136—Advisory Action dated Oct. 10, 2014, 4 pages.

(56) References Cited

OTHER PUBLICATIONS

U.S. Appl. No. 13/660,522—Non-Final Office Action dated Dec. 24, 2013, 9 pages.
U.S. Appl. No. 13/660,522—Final Office Action dated May 30, 2014, 13 pages.
U.S. Appl. No. 13/660,495—Non-final Office Action dated Dec. 26, 2013, 8 pages.
U.S. Appl. No. 13/660,495—Final Office Action dated May 29, 2014, 12 pages.
U.S. Appl. No. 13/660,495—Advisory Action dated Oct. 10, 2014, 4 pages.
Brochure MKT 016 A: iFuse HT Hammertoe Correction Implant, OrthoPro LLC, 2 pages, undated.
Brochure p/n 030-1788 Rev A: ExtremiFuse Hammertoe Fixation System, OsteoMED Small Bone Orthopedics, 6 pages, undated.
Brochure 900-01-008 Rev C: Hammer Toe Implant System Instructions for Use, Trilliant Surgical Ltd, 2 pages, undated.
Bensmann, et al., "Nickel-titanium Osteosynthesis Clips," Reprint from Medical Focus, 1983.
Besselink, Sachdeva, "Applications of Shape Memory Effects," Memory Metal Holland, Memory Medical Systems, Publication Date Unknown.
Dai, K.R., et al., "Treatment of Intra-Articular Fractures with Shape Memory Compression Staples," Injury, (1993) 24, (IO), 651-655.
Haasters, Dr. J., et al., "The Use of N—Ti As An Implant Material in Orthopedics", pp. 426-444.
Kuo, M.D., et al., "The Use of Nickel-Titanium Alloy in Orthopedic Surgery in China," Orthopedics, Jan. 1989, vol. 12/No. 1.
Lu, M.D., Shibi, "Medical Applications of Ni—Ti Alloys in China," pp. 445-451.
Ricart, "The Use of a Memory Shape Staple in Cervical Anterior Fusion," Proceedings of the Second International Conference on Shape Memory and Superelastic Technologies, Asilomar Conference Center, Pacific Grove, CA, USA, Mar. 2-6, 1997.
Ricart, "The Use of a Memory-Shaple Staple in Cervical Anterior Fusion," in Shape Memory Implants, Springer-Verlag Berlin Heidelberg, 2000.
Tang, Dai, Chen, "Application of a Ni—Ti Staple in the Metatarsal Osteotomy," Bio-Medical Materials and Engineering 6, (1996), 307-312, IOS Press.

\* cited by examiner

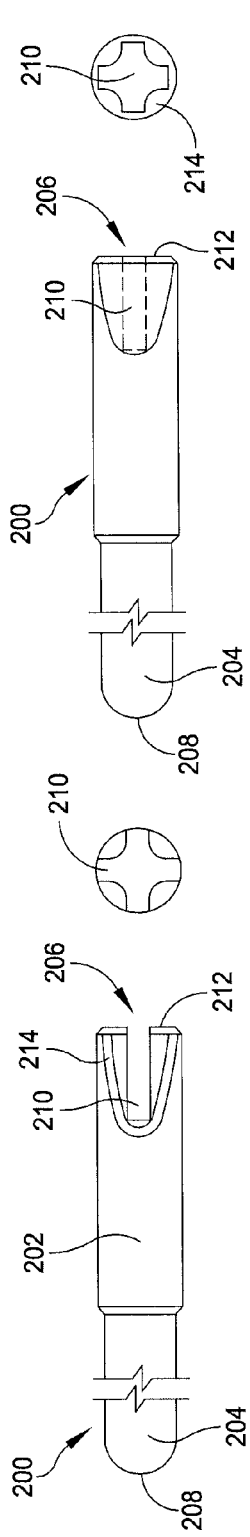

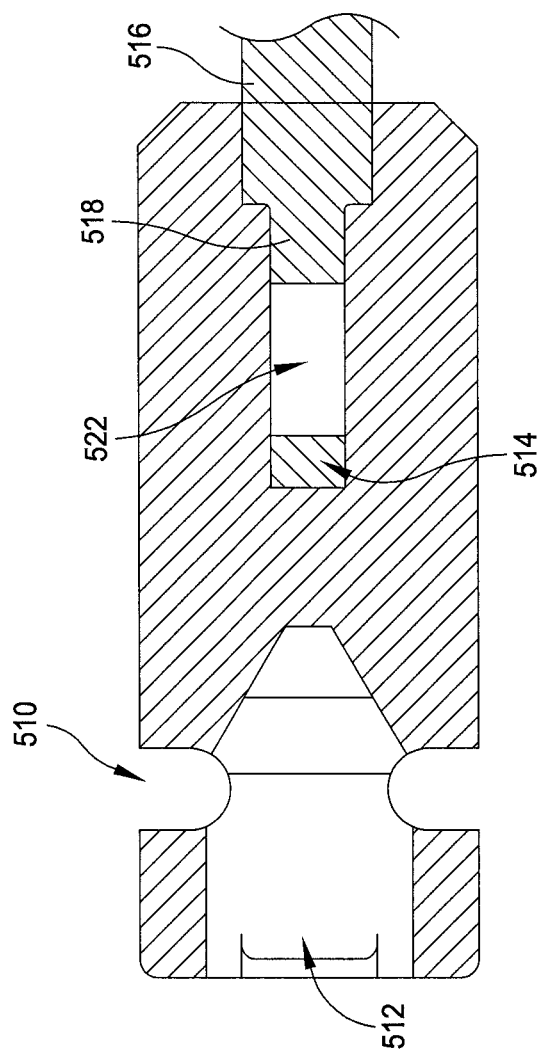
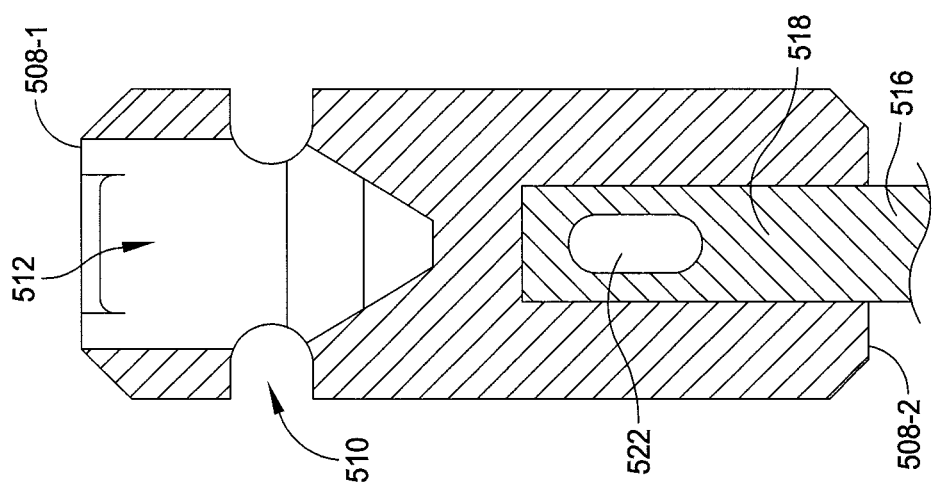
FIG. 22
FIG. 21

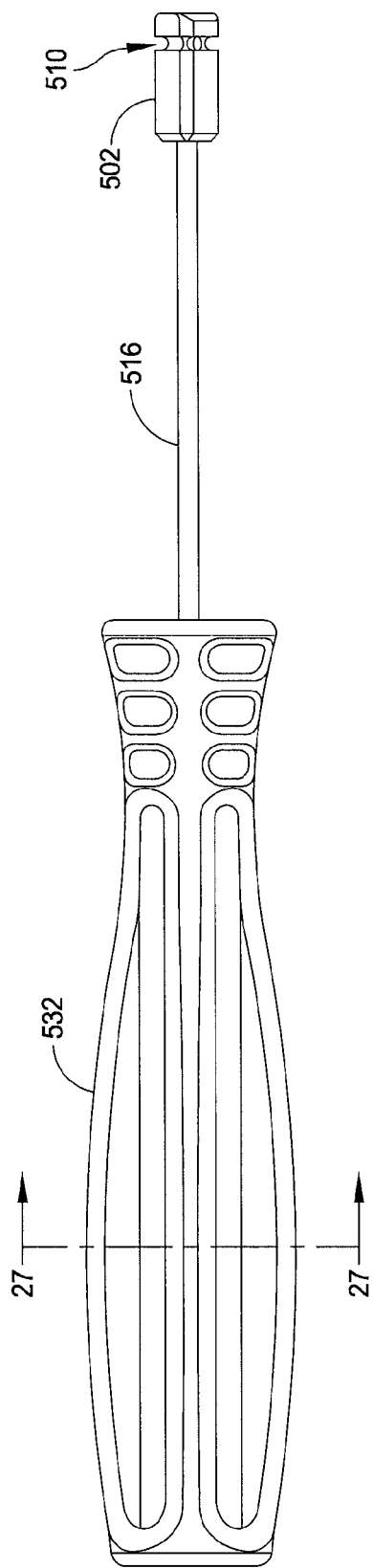
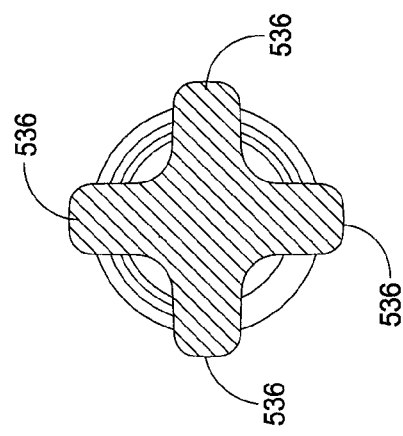
FIG. 26
FIG. 27

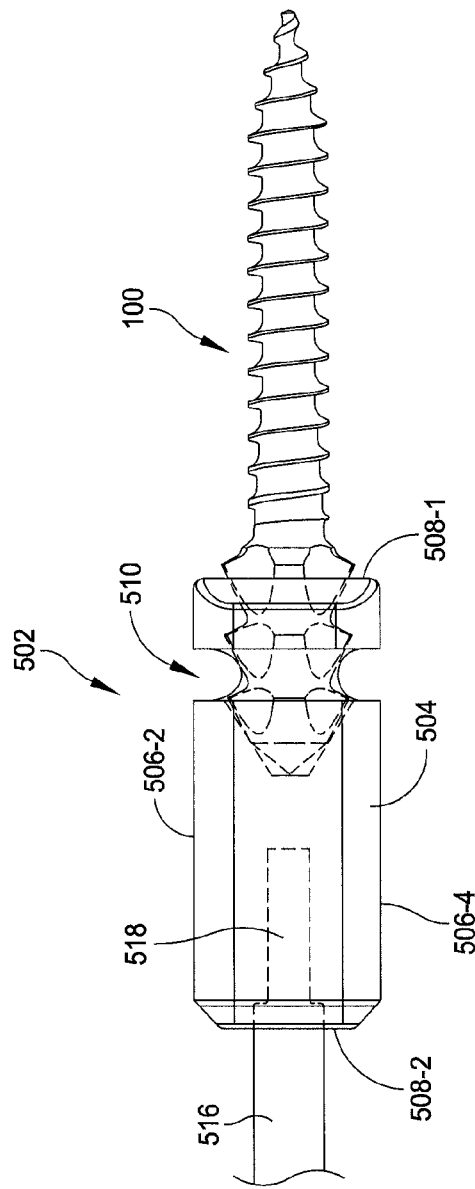
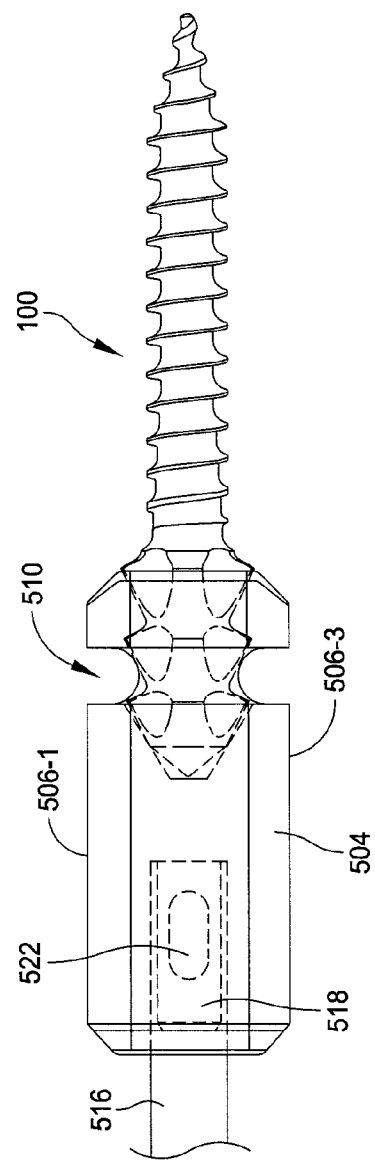
FIG. 28A
FIG. 28B

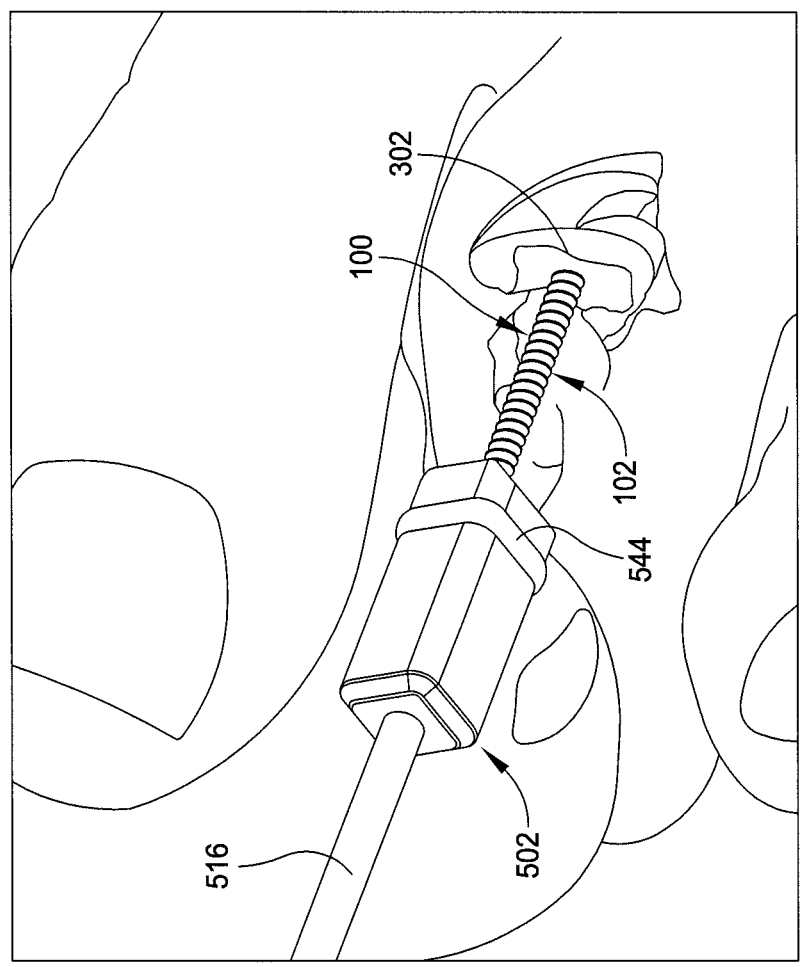

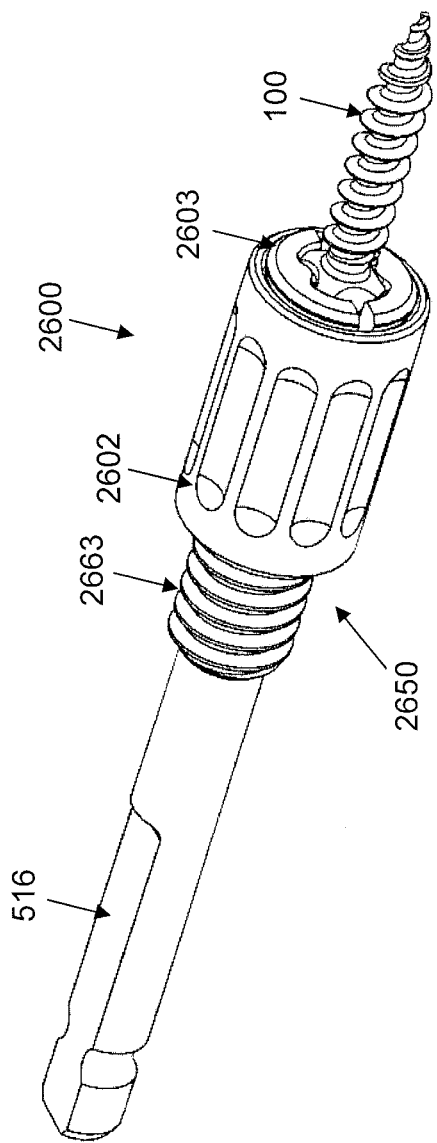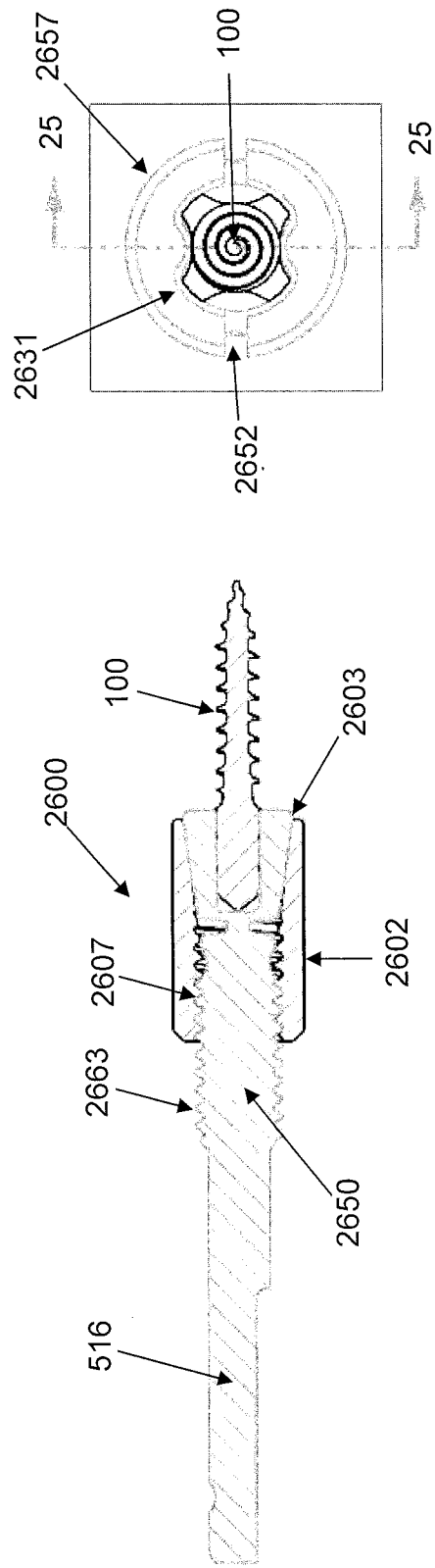
FIG. 35B
FIG. 35D
FIG. 35E

TWO-WIRE TECHNIQUE FOR INSTALLING HAMMERTOE IMPLANT

FIELD OF DISCLOSURE

The disclosed system and method relate implants. More specifically, the disclosed system and method relate to installing an implant for treating hammer toe.

BACKGROUND

Hammer toe is a deformity of the toe that affects the alignment of the bones adjacent to the proximal interphalangeal (PIP) joint. Hammer toe can cause pain and can lead to difficulty in walking or wearing shoes. A hammer toe can often result in an open sore or wound on the foot. In some instances, surgery can be required to correct the deformity by fusing one or both of the PIP and distal interphalangeal (DIP) joints.

The most common corrective surgery includes the placement of a pin or rod in the distal, middle, and proximal phalangees of the foot to fuse the PIP and DIP joints. The pin or rod is cut at the tip of the toe, externally of the body. A plastic or polymeric ball is placed over the exposed end of the rod, which remains in the foot of the patient until the PIP and/or DIP joints are fused in approximately 6 to 12 weeks. This conventional treatment has several drawbacks such as preventing the patient from wearing closed toe shoes while the rod or pin is in place, and the plastic or polymeric ball can snag a bed sheet or other object due to it extending from the tip of the toe resulting in substantial pain for the patient.

Another conventional implant includes a pair of threaded members that are disposed within adjacent bones of a patient's foot. The implants are then coupled to one another through male-female connection mechanism, which is difficult to install in situ and has a tendency to separate.

Yet another conventional implant has body including an oval head and a pair of feet, which are initially compressed. The implant is formed from nitinol and is refrigerated until it is ready to be installed. The head and feet of the implant expand due to the rising temperature of the implant to provide an outward force on the surrounding bone when installed. However, the temperature sensitive material can result in the implant deploying or expanding prior to being installed, which requires a new implant to be used.

Accordingly, an improved implant for treating hammer toe is desirable.

SUMMARY

In some embodiments, a method includes inserting a first surgical device into an exposed first end of a first bone until a trailing end of the first surgical device is disposed adjacent to the first end of the first bone. A second surgical device is inserted into an exposed first end of a second bone while the first surgical device remains disposed within the first bone. A first portion of an implant is advanced into the second bone while being engaged with a passageway defined by the implant such that the implant is guided by the second surgical device. The second surgical device is removed from the second bone and from its engagement with the implant. The first bone is repositioned such that the first surgical device is aligned with the passageway defined by the implant, and the first bone is forced into engagement with a second portion of the implant.

In some embodiments, a method includes forming an incision to gain access to a joint between first and second bones, flexing the first and second bones such that the first and second bones are disposed at an angle with respect to one another, inserting a first surgical device into the first bone until a first end of the first surgical device is disposed adjacent to a first end of the first bone, and inserting a second surgical device into the second bone while the first surgical device remains disposed within the first bone. A first portion of an implant is advanced into the second bone while a passageway defined by the implant is engaged with the second surgical device such that the implant is guided by the second surgical device. The second surgical device is removed from the second bone and from its engagement with the implant. The first bone is repositioned such that the first surgical device is aligned with the passageway defined by the defined by the implant, and the first bone is forced into engagement with a second portion of the implant.

In some embodiments, a surgical method includes gaining access to a joint between a middle phalange and a proximal phalange, inserting a first end of a first surgical device into a proximal end of the middle phalange, advancing the first surgical device into the middle phalange and a distal phalange until a second end of the first surgical device is disposed adjacent to the proximal end of the middle phalange, and inserting a first end of a second surgical device into a distal end of the proximal phalange while the first surgical device remains disposed within the middle and distal phalanges. A first portion of an implant is advanced into the proximal phalange using the second surgical device as a guide. The second implant is removed. The first surgical device is inserted into a passageway defined by the implant while the first surgical device remains disposed within the middle and distal phalange, and the first surgical device is removed from its engagement with the implant, middle phalange, and distal phalange.

BRIEF DESCRIPTION OF THE DRAWINGS

These and other features and advantages of the present invention will be more fully disclosed in, or rendered obvious by the following detailed description of the preferred embodiments of the invention, which are to be considered together with the accompanying drawings wherein like numbers refer to like parts and further wherein:

FIG. 7 is a side view of one example of a driving adapter for use with the hammer toe implants illustrated in FIGS. 1 and 6;

FIG. 8 is an end view of the driving adapter illustrated in FIG. 7;

FIG. 9 is a side view of another example of a driving adapter for use with the hammer toe implants illustrated in FIGS. 1 and 6;

FIG. 10 is an end view of the driving adapter illustrated in FIG. 9;

FIG. 11A is an assembly view of a hammer toe implant engaged by a driving adapter;

FIG. 11B is an assembly view of a cannulated hammer toe implant engaged by a cannulated driving adapter;

FIG. 21 is a cross-sectional view of the adapter taken along line 21-21 in FIG. 20;

FIG. 22 is a cross-sectional view of the adapter taken along line 22-22 in FIG. 20;

FIG. 26 is a plan view of driving assembly illustrated in FIG. 17 without the o-ring;

FIG. 27 is a cross-sectional view of the handle taken along line 27-27 in FIG. 26;

FIG. 28A illustrates an implant coupled to the adapter of the driving assembly illustrated in FIG. 17;

FIG. 28B illustrates an implant coupled to the adapter of the driving assembly illustrated in FIG. 17;

FIG. 29 illustrates a hammer toe implant being driven into a proximal phalange;

FIG. 35B is an isometric view of some embodiments of an implant kit comprising an adapter that is configured for coupling to an hammer toe implant using a collet and showing a hammer toe implant received in the adapter;

FIG. 35D is a an end view of the implant kit illustrated in FIG. 35B;

FIG. 35E is cross-sectional view of the implant kit taken along line 25-25 in FIG. 35D;

DETAILED DESCRIPTION

Figure 1:
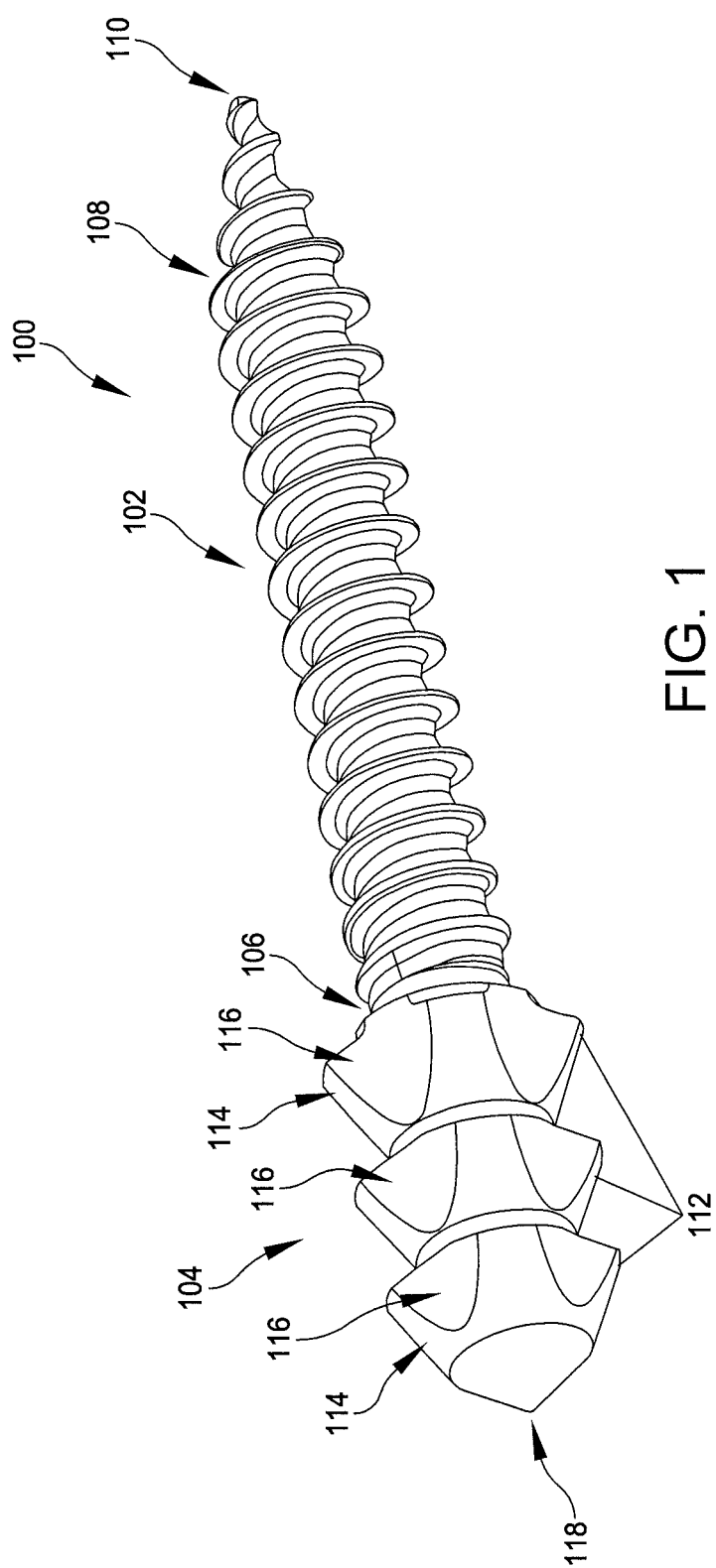
FIG. 1 is an isometric view of an improved hammer toe implant according to some embodiments.

This description of preferred embodiments is intended to be read in connection with the accompanying drawings, which are to be considered part of the entire written description. The drawing figures are not necessarily to scale and certain features of the invention can be shown exaggerated in scale or in somewhat schematic form in the interest of clarity and conciseness. In the description, relative terms such as "horizontal," "vertical," "up," "down," "top," and "bottom" as well as derivatives thereof (e.g., "horizontally," "downwardly," "upwardly," etc.) should be construed to refer to the orientation as then described or as shown in the drawing figure under discussion. These relative terms are for convenience of description and normally are not intended to require a particular orientation. Terms including "inwardly" versus "outwardly," "longitudinal" versus "lateral," and the like are to be interpreted relative to one another or relative to an axis of elongation, or an axis or center of rotation, as appropriate. Terms concerning attachments, coupling, and the like, such as "connected" and "interconnected," refer to a relationship wherein structures are secured or attached to one another either directly or indirectly through intervening structures, as well as both movable or rigid attachments or relationships, unless expressly described otherwise. The term "operatively connected" is such an attachment, coupling or connection that allows the pertinent structures to operate as intended by virtue of that relationship.

FIG. 1 illustrates one example of an improved implant 100 for treating hammer toe. As shown in FIG. 1, implant 100 includes a threaded portion 102 and a blade portion 104, which are connected together at an engagement portion 106. In some embodiments, implant 100 has a substantially linear geometry. In some embodiments, implant 100 has an overall length of approximately 19 mm (approximately 0.75 inches) (e.g. 18.9-19.1 mm (0.74-0.76 inches)). In some embodiments, blade portion 104 can be disposed at angle with respect to a longitudinal axis defined by the threaded portion 102. The angle can be between zero and 45 degrees, and more particularly between approximately five and fifteen degrees, although one skilled in the art will understand that implant 100 can have other dimensions and be provided in different sizes. For example, implant 100 can be provided in lengths of 16 mm and 22 mm, to name a few potential lengths.

In some embodiments, threaded portion 102 includes a plurality of threads 108 disposed along its entire length, which can be approximately 13 mm (approximately 0.5 inches) (e.g. 12.9-13.1 mm (0.49-0.51 inches)) although one skilled in the art will understand that threaded portion 102 can have other dimensions and be provided in different sizes. For example, threaded portion 102 can be provided in lengths of 10 mm and 15 mm, to name a few potential lengths. The tip 110 of threaded portion 102 can be pointed to facilitate the advancement of threads 108 into bone. Threads 108 can have a maximum outer diameter of approximately 2 mm (approximately 0.08 inches), although one skilled in the art will understand that thread portion 102 can have other dimensions and be configured to be received within a phalange bone of a person. For example, threads can have an outer diameter of approximately 2.4 mm and 1.6 mm, to name a few potential possibilities.

Figure 2:
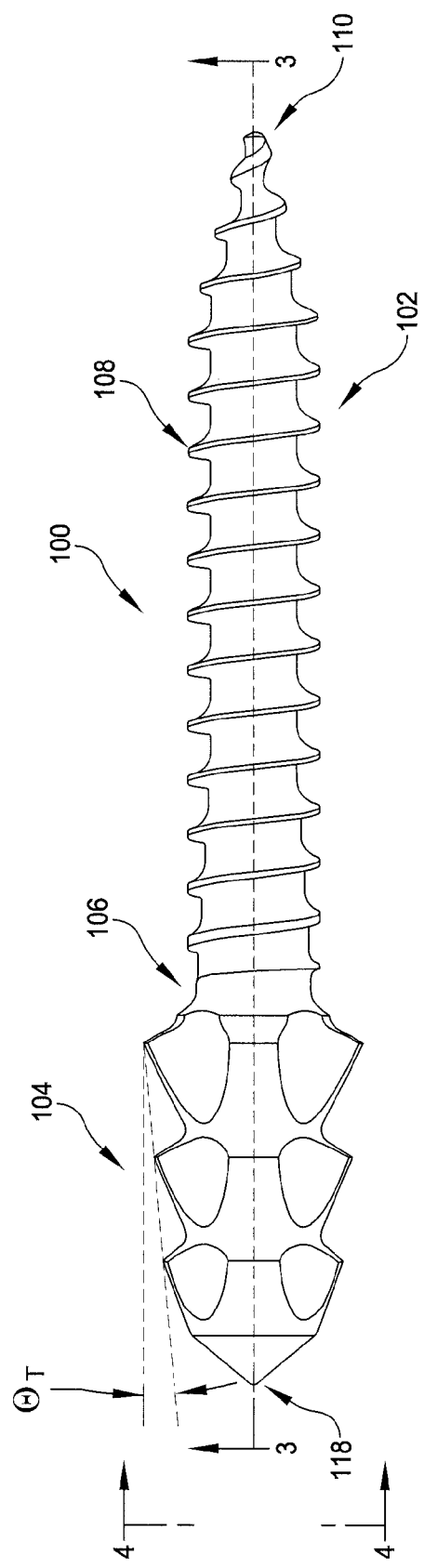
FIG. 2 is a top side view of the hammer toe implant illustrated in FIG. 1.
Figure 3:
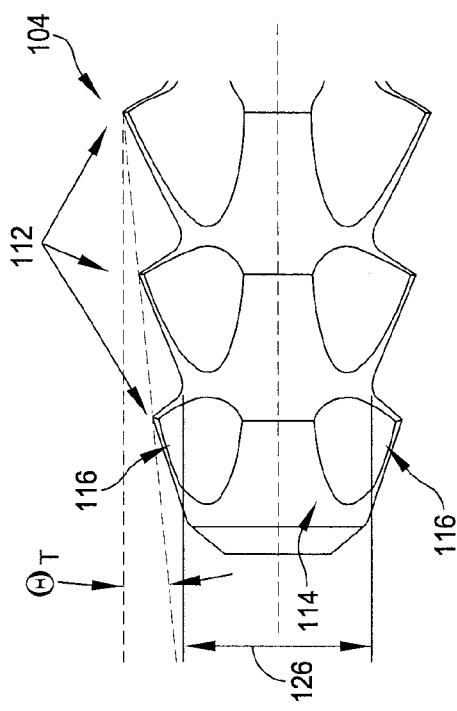
FIG. 3 is a top side view of the blade portion of the hammer toe implant illustrated in FIG. 6.
Figure 4:
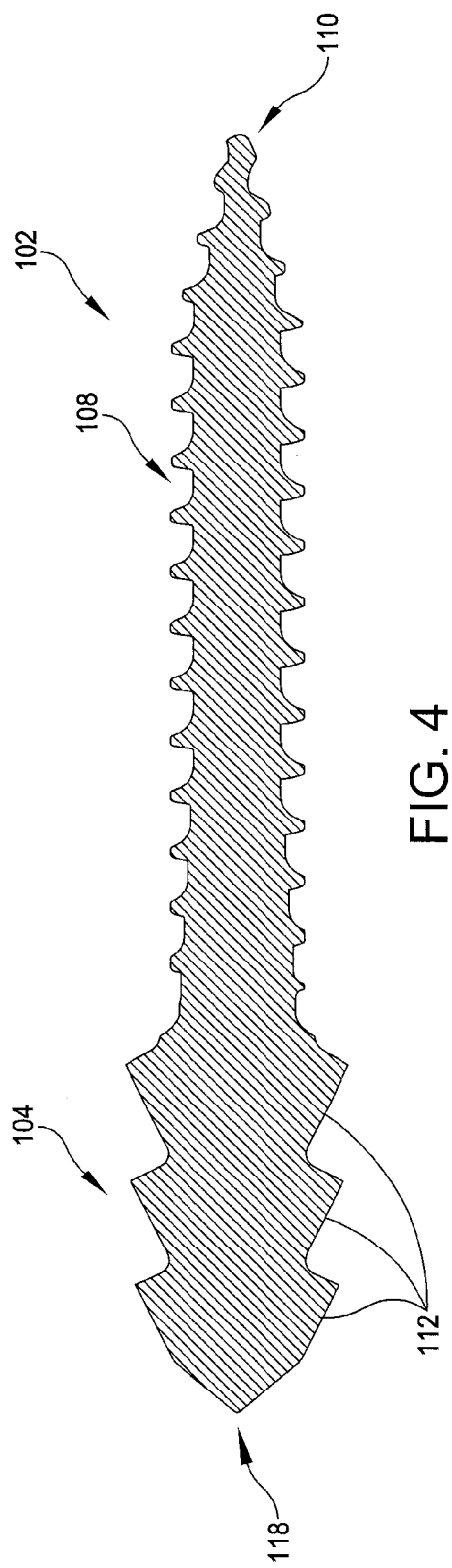
FIG. 4 is a sectional view of the hammer toe implant taken along line 3-3 in FIG. 2.

As shown in FIGS. 1-4 and 6, blade portion 104 can have a substantially cylindrical cross-sectional geometry. One skilled in the art will understand that blade portion 104 can have other cross-sectional geometries. In some embodiments, blade portion 104 can have a taper defined by a plurality of blades 112. For example, as best shown in FIGS. 2 and 3, the taper of blade portion 104 can be at an angle relative to the longitudinal axis defined by the elongated central portion of implant 100. In some embodiments, the taper is at an angle ($\theta_T$) between 1 and 10 degrees relative to the longitudinal axis defined by the elongated central portion of implant 100. For example, the taper can be at an angle ($\theta_T$) of approximately 5 degrees (e.g. 4.9-5.1 degrees) degrees relative to the longitudinal axis defined by the elongated central portion of implant 100. In some embodiments, blade portion 104 includes a taper along its diameter defined by the plurality of blades 112. In the illustrated embodiments of FIGS. 2, 3 and 5, the plurality of blades 112 include a first blade 112 having a first diameter disposed proximate the engagement portion 106 and a second blade 112 having a second diameter smaller than the first diameter disposed proximate a terminating end 118 of the blade portion 104. In some embodiments, the first diameter can be approximately 5 mm (approximately 0.20 inches) (e.g. 4.9-5.1 mm) (0.19-0.21 inches) and the second diameter can be approximately 4.5 mm (approximately 0.18 inches) (e.g. 4.4-4.6 mm) although one skilled in the art will understand that the plurality of blades 112 can have other diameters and other dimensions. For example, the first diameter can be provided as in lengths of 4 mm and 6 mm, to name a few potential diameters. The inventors have found that the tapered blade portion 104 permits each successive blade 112 of blade portion 104 to achieve interference with bone during insertion which enhances fixation of the blade portion 104 compared to a non-tapered blade portion 104. In the illustrated embodiment, the blades 112 of blade portion 104 include a valley 126 between blades 112 and the teeth portions 114 of each blade 112. In some embodiments, valley 126 of teeth portions 114 of each blade 112 is substantially the same. In other embodiments, the valleys 126 of teeth portions 114 vary as the respective diameters of the successive blades are tapered.

In some embodiments, the terminating end 118 of blade portion 104 is a point, although one skilled in the art will understand that blade portion 104 can have a terminating end of other dimensions, sizes and/or shapes. In the illustrated embodiment of FIGS. 3 and 6, the terminating end 118 of blade portion 104 is cannulated. In various embodiments (FIGS. 3 and 6), the blade portion 104 and threaded portion 102 of implant 100 are cannulated. In some embodiments, implant 100 (FIGS. 3, 6, 11B) includes a groove 109 sized and configured to receive a k-wire, pin, or other surgical device or instrument that extends along the length of implant 100 in a direction that is parallel to a longitudinal length defined by implant 100. In some embodiments, the taper of blade portion 104 can be defined by the plurality of blades 112 having successively smaller diameters between a blade 112 disposed proximate engagement portion 106 and a blade 112 disposed proximate terminating end 118 of the blade portion 104.

Figure 5:
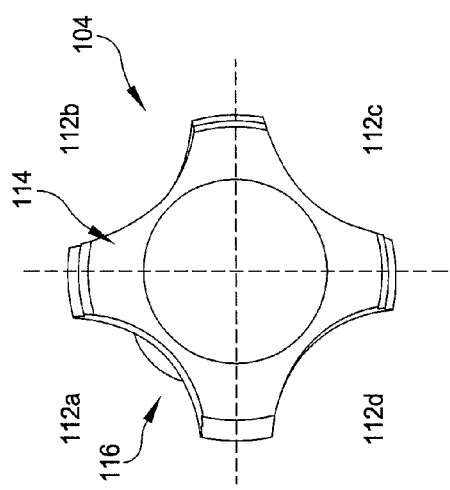
FIG. 5 is an end on view of the hammer toe implant taken along line 4-4 in FIG. 2.

In various embodiments, each blade 112 of the plurality of blades 112 of blade portion 104 include a plurality of grooved portions 116 and a plurality of teeth portions 114 to form a substantially cruciform cross-sectional geometry (FIG. 5). In the illustrated embodiment of FIG. 5, each blade 112 of blade portion 104 having a substantially cylindrical cross-section includes a plurality of substantially rounded grooved portions 116 formed along an axis parallel to a longitudinal axis of blade portion 104 and a plurality of teeth portions 114. As shown in FIGS. 1-5 and 6, blade portion 104 can have a substantially cylindrical cross-sectional geometry including a plurality of blades 112 having respective substantially cruciform cross-sectional geometries defined by a grooved portion 116 being disposed in each quadrant (112a-d) of each blade 112. In some embodiments, each blade 112 of blade portion 104 includes a pair of opposing grooved portions 116 (e.g. in quadrants 112b and 112d and in quadrants 112a and 112c respectively) to form a substantially cruciform cross-sectional geometry. As shown in FIG. 5, the grooved portions 116 of each pair of opposing grooved portions 116 (e.g. in quadrants 112a and 112c and 112b and 112d respectively) are substantially symmetrical. In the illustrated embodiment of FIG. 5, the grooved portions 116 disposed in each quadrant (112a-d) of each blade 112 are substantially symmetrical and the teeth portions 114 of each blade 112 are substantially symmetrical.

As shown more clearly in the illustrated embodiments of FIGS. 1, 3, 5 and 6, each blade 112 of blade portion 104 includes no flat surfaces. In some embodiments, a centerline of grooved portion 116 of each blade 112 of blade portion 104 is dimensioned such that it is tangent to respective diameters measured at the intersections of grooved portion 116 and the respective teeth portions 114. In the illustrated embodiments, grooved portions 116 are concave in shape and teeth portions 114 are convex in shape. In the illustrated embodiments, the respective surfaces of each blade 112 are rounded. In some embodiments, teeth portions 114 are serrated.

Figure 6:
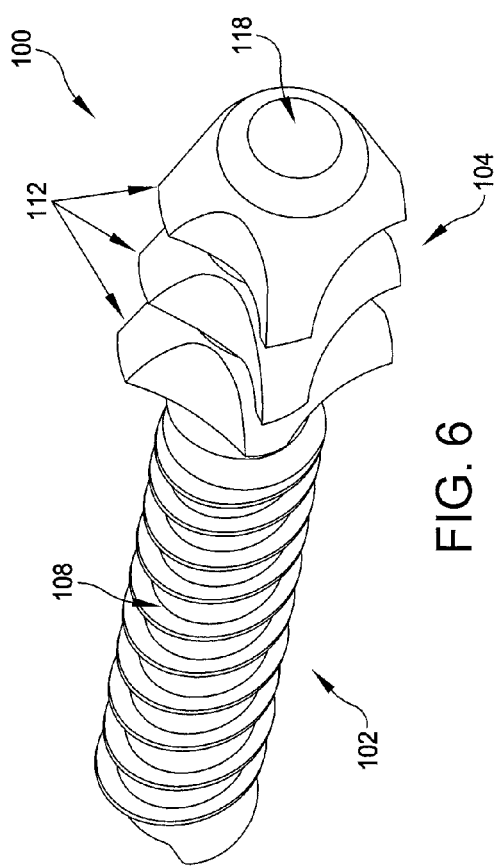
FIG. 6 is an isometric view of an improved, cannulated hammer toe implant according to some embodiments.

In some embodiments, engagement portion 106 can include a pair of protrusions extending from opposite sides of implant 100 and having rounded outer edges. In some embodiments, for example as shown in FIG. 2, the sides of the protrusions of engagement portion 106 can be substantially parallel with each other. In some embodiments, at least a portion of the implant 100 is cannulated (FIGS. 3, 6). The inventors have found that a cannulated implant 100 design can permit surgeons to stabilize joints (e.g. a metatarsal phalangeal joint (MPJ)) during a surgical procedure.

Implant 100 is configured to be installed using a driving adapter 200 such as the one illustrated in FIGS. 7-10. The driving adapter 200 has an elongated body 202 having a proximal end 204 and a distal end 206. Body 202 of driving adapter 200 can have a circular cross-sectional geometry, although one skilled in the art will understand that body 202 can have other cross-sectional geometries including, but not limited to, triangular, rectangular, pentagonal, and hexagonal to name a few.

Proximal end 204 can be substantially solid and have a rounded tip 208. In some embodiments, proximal end 204 and distal end 206 can be cannulated such as, for example, to receive a k-wire. Distal end 206 can define a slot 210 sized and configured to receive blade portion 104 of implant 100 therein. In some embodiments, slot 210 can have a cylindrical cross-sectional geometry and have a depth that is sufficient to receive the entire blade portion 104 of implant 100 such that distal edges 212 of slot 210 contact the protrusions of engagement portion 106. In some embodiments, slot 210 can have a cylindrical, cruciform cross-sectional geometry and have a depth that is sufficient to receive the entire blade portion 104 of implant 100 such that distal edges 212 of slot 210 contact the protrusions of engagement portion 106. However, one skilled in the art will understand that slot 210 can have other cross-sectional geometries and dimensions. Slot 210 can extend through side walls 214 of body 202 as shown in FIGS. 7 and 8, or side walls 214 can completely enclose slot 210 as shown in FIGS. 9 and 10.

If the driving adapter 200 is to be used with an implant 100 having a substantially linear lengthwise geometry such as the implant 100 illustrated in FIGS. 1-6, then slot 210 can extend in a direction that is substantially parallel to an axis defined by body 202 of driving adapter 200. If driving adapter 200 is to be used with an implant 100 having a blade portion 104 that extends at an angle with respect to an axis defined by elongated threaded portion 102, then slot 210 can extend from distal edges 212 at an angle with respect to an axis defined by the length of body 202 such that elongated threaded portion 102 of implant 100 is linearly aligned with body 202 of driving adapter 200 as shown in FIGS. 11A and 11B. For example, if blade portion 104 of implant 100 extends at a ten degree angle with respect to an axis defined by elongated threaded portion 102, then slot 210 of driving adapter 200 can extend at a ten degree angle with respect to a longitudinal axis defined by body 202 such that threaded portion 102 of implant 100 and body 202 of driving adapter 200 are substantially linearly aligned.

Figure 12B:
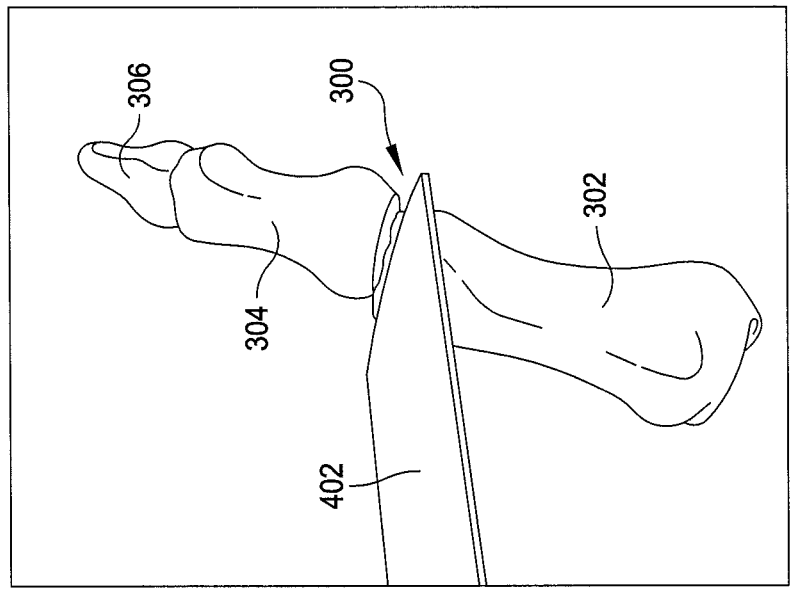
FIG. 12B illustrates the middle and proximal phalangees of a foot being resected.
Figure 12A:
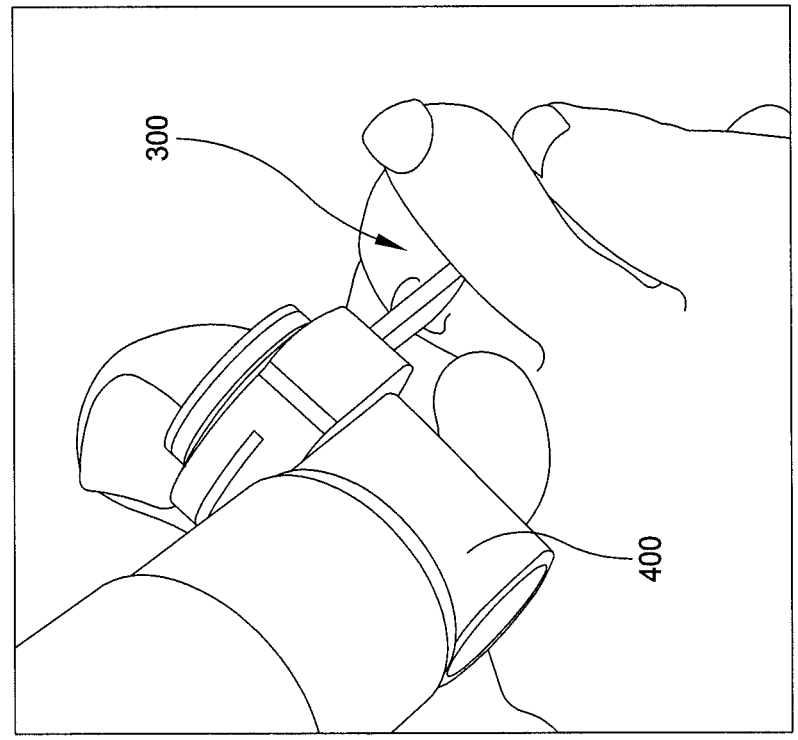
FIG. 12A illustrates the middle and proximal phalangees of a foot being resected.

A method of installing implant 100 in the proximal interphalangeal joint (PIP) 300 is described with reference to FIGS. 12A-16. However, one skilled in the art will understand that the technique for installing the implant 100 can be applied to other joints such as, for example, the distal interphelangeal (DIP) joint between middle phalange 304 and distal phalange 306. As shown in FIGS. 12A and 12B, an incision is made to open the PIP joint 300 and a cutting tool 400 having a blade 402 can be used to resect adjacent faces of proximal phalange 302 and middle phalange 304. The resected surfaces of proximal phalange 302 and middle phalange 304 can be debrided as understood by one skilled in the art.

Figure 13:
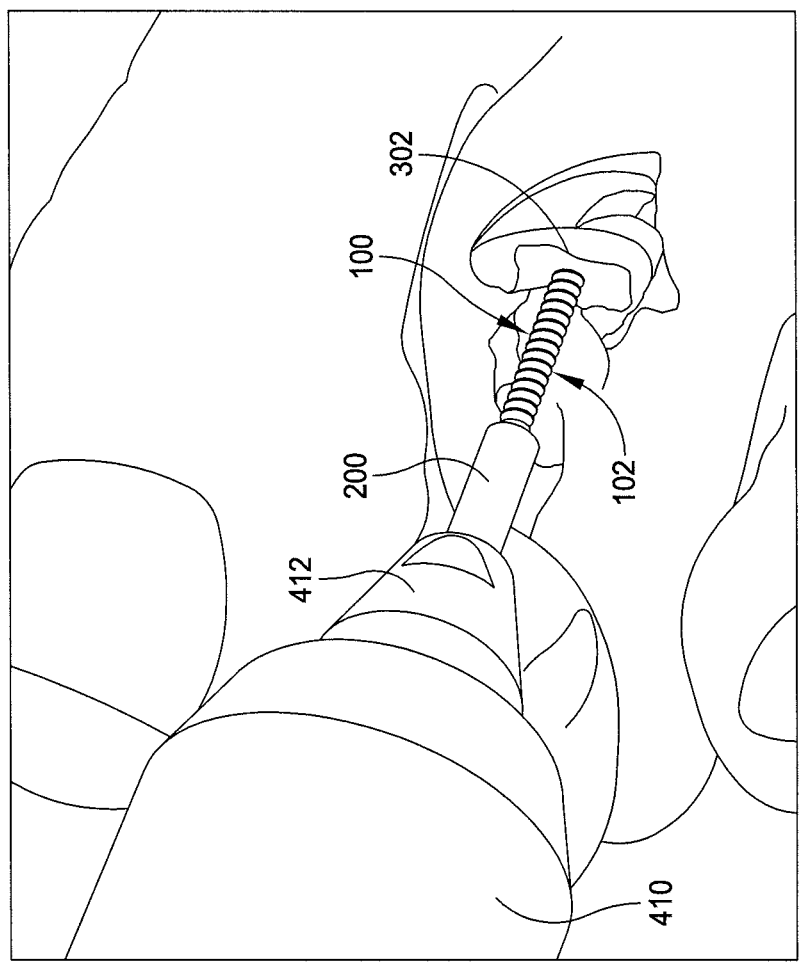
FIG. 13 illustrates a hammer toe implant being driven into a proximal phalange.

Blade portion 104 of implant 100 can be disposed within slot 210 of driving adapter 200 as shown in FIGS. 11A and 11B. In some embodiments, the body 202 of driving adapter 200 can be cannulated. In some embodiments, a k-wire, pin or other suitable surgical device can be inserted into the middle phalange 304 and driven through distal phalange and out of the end of the toe (not shown). A k-wire can be inserted such that a trailing end is disposed within middle phalange 304 or otherwise positioned with respect to the joint such that cannulated implant 100 can be driven into proximal phalange 302. In various embodiments, the body 202 of driving adapter 200 can be secured in a chuck 412 of a drill 410 or other driving instrument as shown in FIG. 13. Drill 410 or other driving instrument is used to drive the threaded portion 102 of implant 100 into the resected surface of proximal phalange 302. With the threaded portion 102 of implant 100 disposed within proximal phalange 302, driving adapter 200 can be disengaged from blade portion 104 of implant 100.

Figure 14:
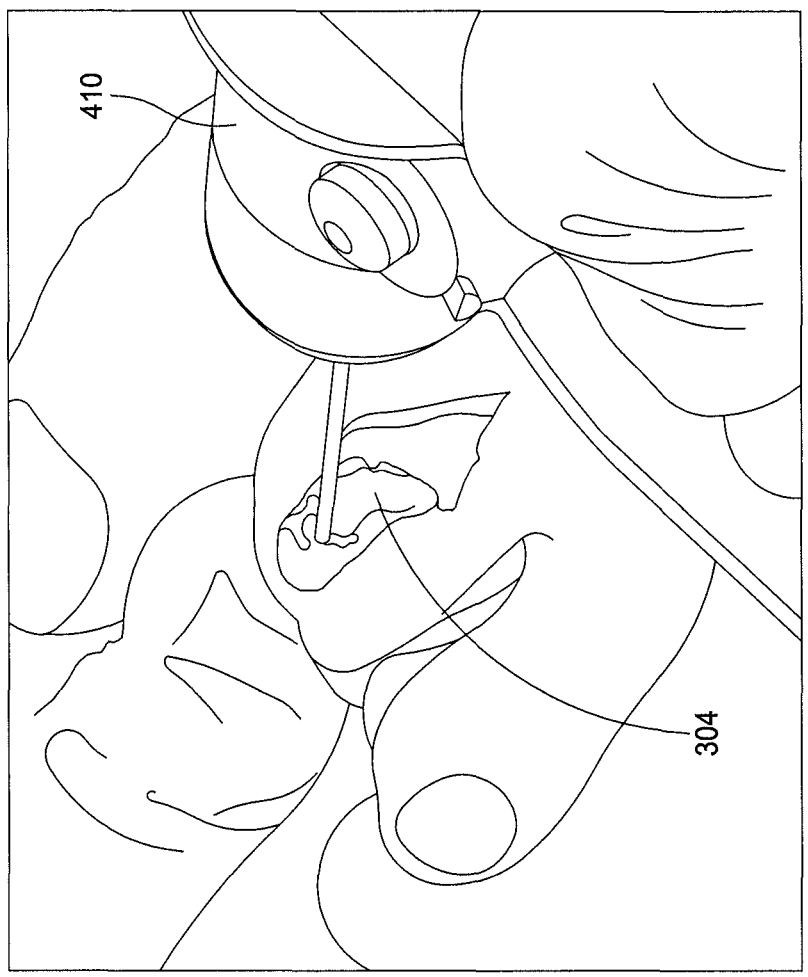
FIG. 14 illustrates a middle phalange being drilled or broached.
Figure 15:
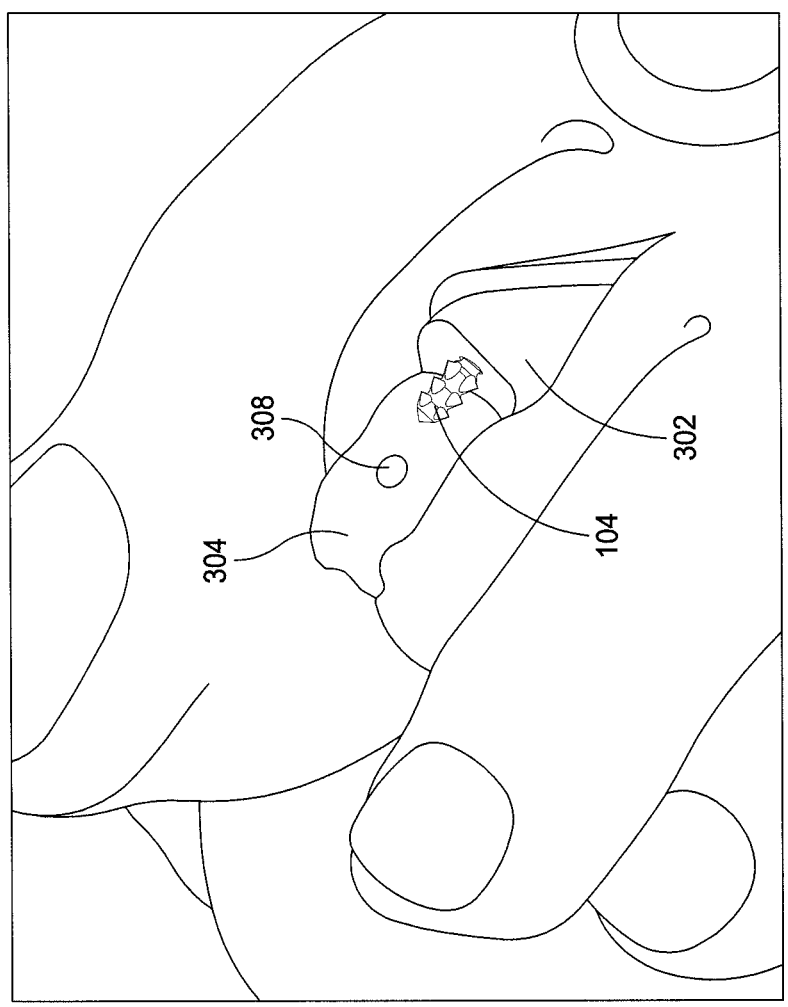
FIG. 15 illustrates a blade of a hammer toe implant extending from the proximal phalange with the middle phalange having been drilled or broached.
Figure 16:
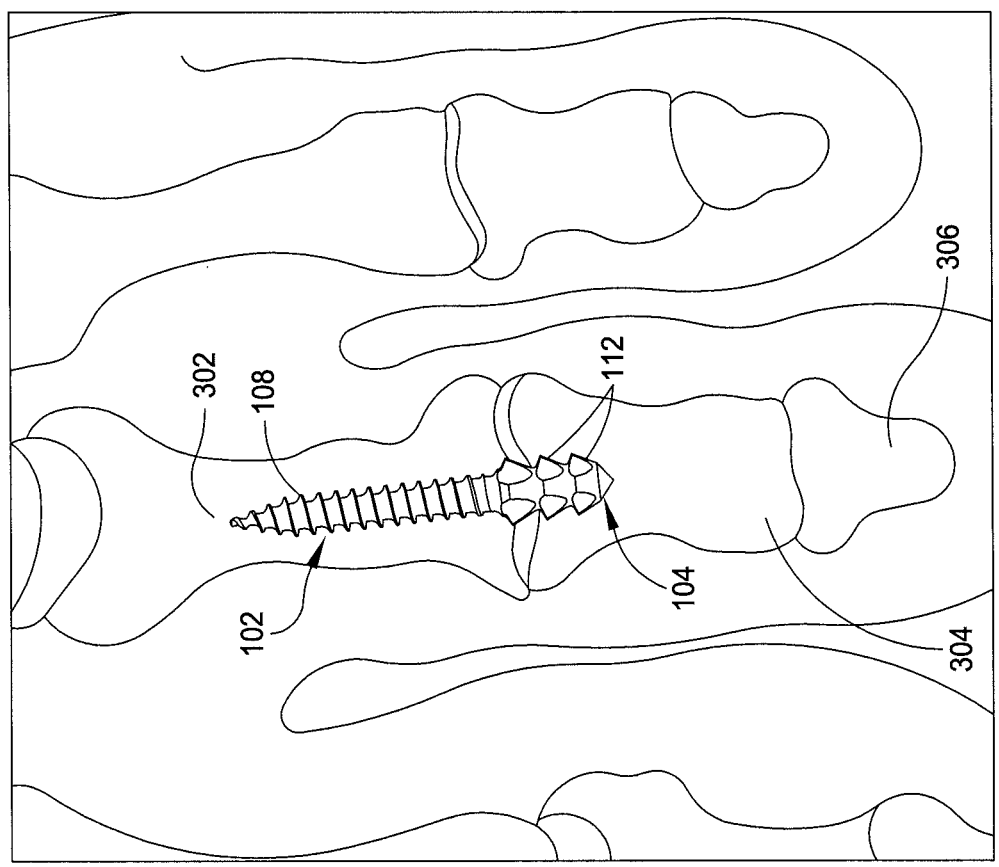
FIG. 16 illustrates a hammer toe implant installed in the middle and proximal phalangees.

Middle phalange 304 can be predrilled or broached using drill 410 to create a hole 308 as shown in FIGS. 14 and 15. The predrilled or broached middle phalange 304 is then repositioned such that the predrilled hole or broach 308 aligns with the blade portion 104 of implant 100. In some embodiments, a dimension (e.g. diameter or width) of the predrilled hole or broach 308 is less than a dimension of blade portion 104 to permit a first blade 112 to achieve interference with the bone and enhance fixation of blade 104. For example, in some embodiments, "valley-to-valley" dimension of blade portion 104 (e.g. the diametrical dimension of blade portion 104 between blades 112). In some embodiments, a k-wire or other suitable surgical device is disposed within middle phalange 304 can be aligned with groove 109 of cannulated implant 100 (FIGS. 3, 6, 11B) disposed within proximal phalange 302. In various embodiments, the middle phalange 304 can be then pressed into engagement with the blade portion 104 as shown in FIG. 16. Serrated teeth portions or edges 114 of blade portion 104 help to maintain the engagement between middle phalange 304 and blade portion 104 of implant 100. In various embodiments, a k-wire or other suitable surgical device can be advanced into the joint, into and through middle phalange 302, into the respective metatarsal and through cannulated implant 100. In various embodiments, the k-wire or other suitable surgical device can remain within the patient for a period of time, e.g. minutes, hours, days or months, and can then be removed to leave behind cannulated implant 100.

Figure 17:
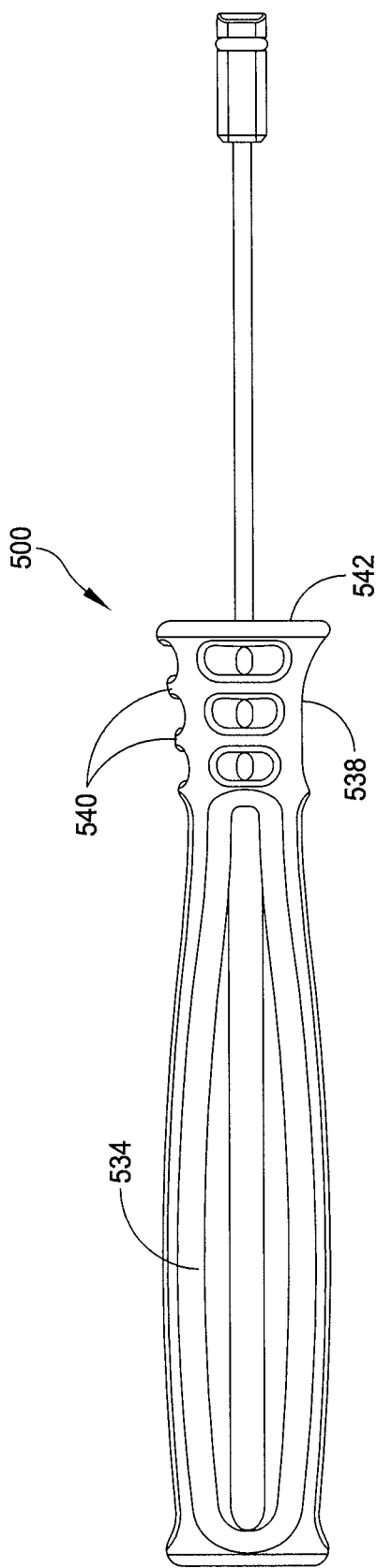
FIG. 17 illustrates another example of a driving assembly for installing an implant.
Figure 18:
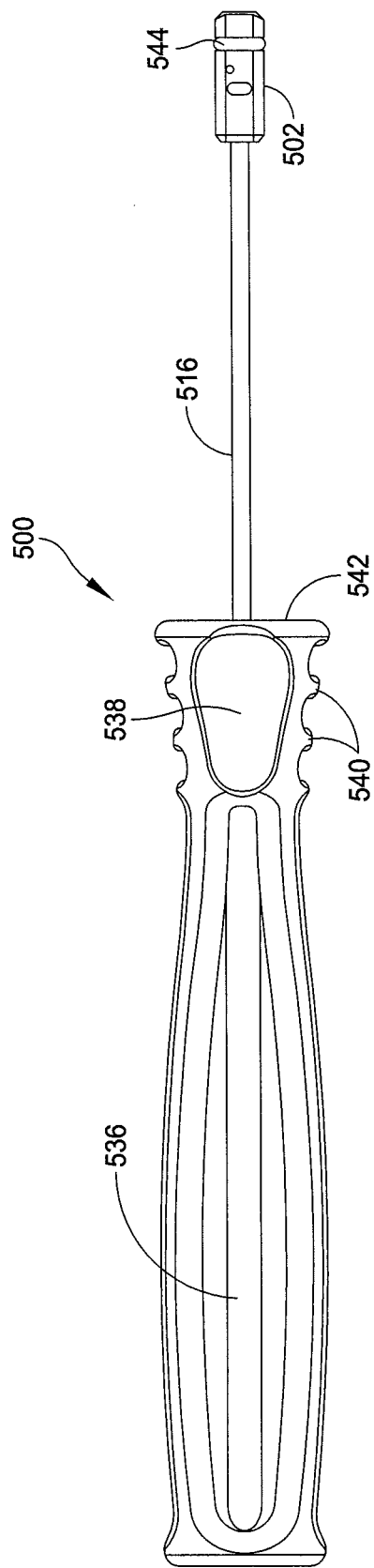
FIG. 18 illustrates a side view of the driving assembly illustrated in FIG. 17.
Figure 20:
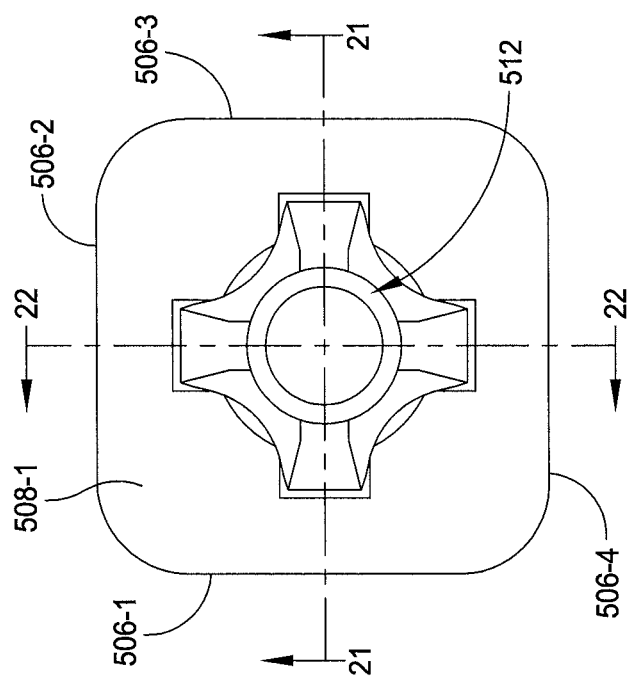
FIG. 20 is an end view of the adapter illustrated in FIG. 19.
Figure 19:
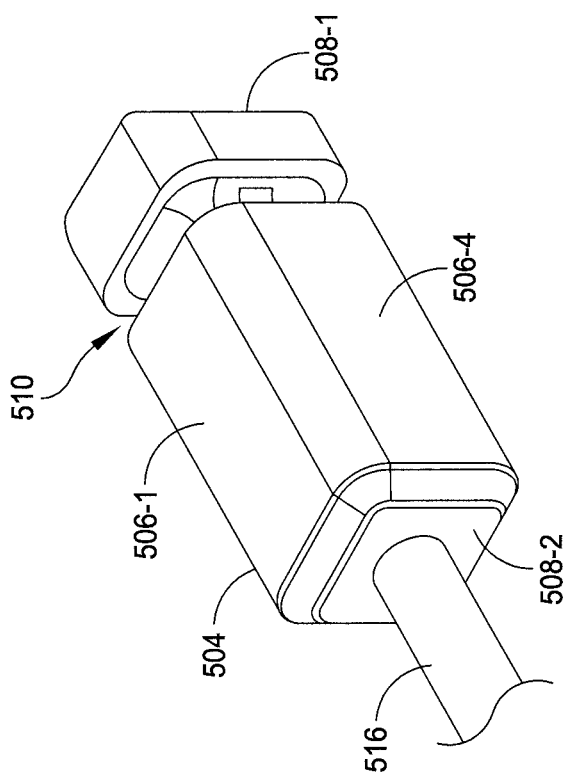
FIG. 19 is an isometric view of an adapter of the driving assembly illustrated in FIG. 17.

FIGS. 17-27 illustrate some embodiments of a driver assembly 500 for installing an implant into bone. As shown in FIGS. 17 and 18, driver assembly 500 includes an adapter 502 coupled to a driving rod 516 onto which a handle 534 is over-molded or otherwise coupled. Adapter 502 includes a body 504 with a substantially rectangular side profile comprising side walls 506-1, 506-2, 506-3, and 506-4 (collectively referred to as "side walls 506") and a pair of end walls 508-1, 508-2 (collectively referred to as "end walls 508") having a substantially square geometry as best seen in FIGS. 19-22.

Body 504 defines a recess 510 along the length of side walls 506. Recess 510 is dimensioned such that an o-ring 544 (FIGS. 17 and 18) can be received therein. Additionally, recess 510 is located along side walls 506 at a distance from end walls 508 such that recess 510 is aligned with a valley 126 of teeth portions 114 along the circumference of blade portion 104.

End wall 508-1 defines an aperture 512 (FIG. 20) having a geometry that complements the cross-sectional geometry of blade portion 104 of implant 100. For example, if implant 100 has a cylindrical, cruciform straight blade portion 104 as illustrated in FIG. 2, then aperture 512 can extend approximately parallel to the lengthwise direction of side walls 506 (FIGS. 21-22). If the blade portion 104 of implant 100 is angled (not shown), then aperture 512 can extend from wall 508-1 at an angle relative to the plane defined by side wall 506-2 or 506-4 as will be understood by one skilled in the art. In some embodiments, aperture 512 has a depth that is greater than or equal to a length of blade portion 104 such that blade portion 104 can be received within body 504 and engagement portion 106 abuts end wall 508-1. Similarly, end wall 508-2 defines an aperture that is sized and configured to receive an end of elongated driving rod 516 therein.

Figure 23:
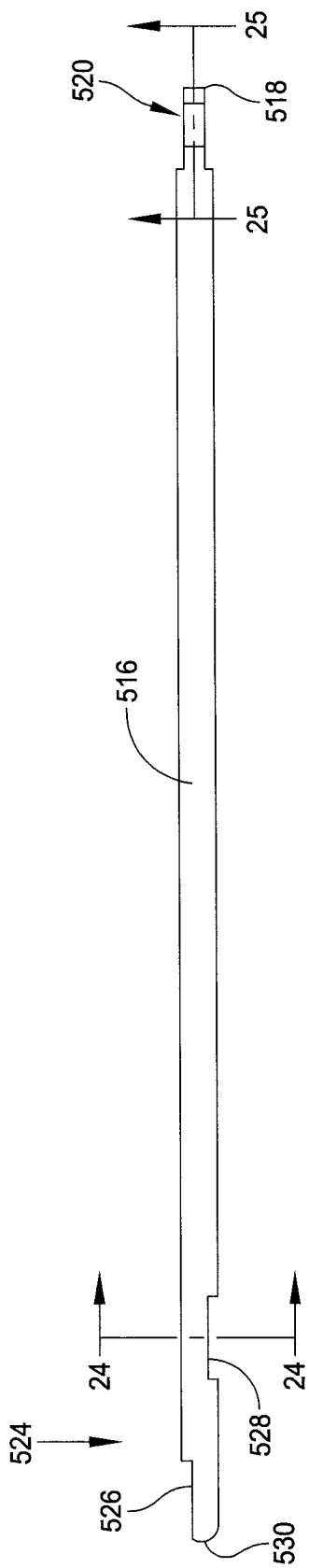
FIG. 23 is a plan view of the driving rod of the driving assembly illustrated in FIG. 17.
Figure 25:
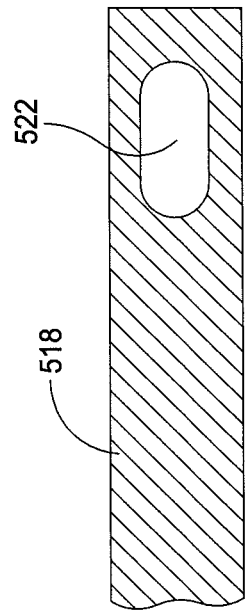
FIG. 25 is a cross-sectional view of the fin of the driving rod taken along line 25-25 in FIG. 23.
Figure 24:
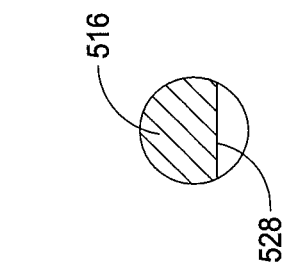
FIG. 24 is a cross-sectional view of the driving rod taken along line 24-24 in FIG. 23.

As best seen in FIGS. 23-25, driving rod 516 includes a fin 518 disposed at a first end 520. Fin 518 disposed at end 520 of driving rod 516 has a rectangular shape and is sized and configured to be received within aperture 512 of adapter 502. Fin 518 defines a slot 522, which is sized and configured to receive a pin (not shown) for cross-pinning driving rod 516 to adapter 502. In some embodiments, end 520 can have other cross-sectional geometries including, but not limited to, triangular, square, and pentagonal, to name a few possibilities, that are configured to be received within aperture 514. Adapter 502 can be over-molded onto the end of driving rod 516. However, one skilled in the art will understand that adapter 502 can be cross-pinned or otherwise coupled to driving rod 516.

The opposite end 524 of driving rod 516 defines a pair of flats 526, 528, which are disposed on opposite sides of driving rod 516. As best seen in FIG. 23, flat 526 extends from tip 530 and is linearly spaced from flat 528, which is disposed at a greater distance from tip 530 than flat 526. However, one skilled in the art will understand that flats 526, 528 can be disposed at other positions along driving rod 516. Flats 526, 528 are configured to provide a contact surface for coupling to handle 532 (FIG. 26), which can be over-molded onto driving rod 516, such that rotation of handle 532 is translated to driving rod 516.

Turning now to FIGS. 26 and 27, handle 532 has an elongated body 534 that includes a plurality of ribs 536 that extend in a longitudinal direction along body 534 to provide a gripping surface for a user. As best seen in FIGS. 17 and 22, a smooth surface 538 interrupts circumferential ridges 540, which are disposed adjacent to proximal end 542 also for providing a gripping surface for a user.

Driver assembly 500 can be provided in a kit with a first adapter 502 for use with a straight implant 100 and a second adapter for use with an angled implant 100. A plurality of implants 100 of different sizes can also be provided in the kit. The kit can be used in an operation similar to the operation described above with respect to FIGS. 12A-16.

Blade portion 104 of implant 100 is disposed within aperture 512 of adapter 502 as shown in FIGS. 28A and 28B. With blade portion 104 disposed within aperture 512, an o-ring 544 (FIGS. 17 and 18) is placed in recess 510 defined by adapter 502 and within a valley 126 of serrated edges 112 along the top and bottom sides 114, 116 of blade portion 104. O-ring 544 secures implant 100 to adapter 502 such that implant does not move axially out of aperture 512.

Once implant 100 is secured to adapter 502, the surgeon uses handle 534 to manually drive threaded portion 102 of implant 100 into the resected surface of proximal phalange 302 as illustrated in FIG. 29. Implant 100 is driven into proximal phalange 302 until engagement portion 106 abuts proximal phalange 302. Implant 100 is decoupled from adapter 502 by axially pulling handle 534 away from implant 100 with sufficient force to flex o-ring 544 and separate adapter 502 from implant 100.

Middle phalange 304 can be predrilled or broached using drill 410 to create a hole 308 as shown in FIGS. 14 and 15.

The predrilled or broached middle phalange 304 is then repositioned such that the predrilled hole or broach 308 aligns with the blade portion 104 of implant 100. The middle phalange 304 is then pressed into engagement with the blade portion 104 as shown in FIG. 16. Serrated teeth portions 114 of blade portion 104 help to maintain the engagement between middle phalange 304 and blade portion 104 of implant 100.

The implant described above can advantageously be installed through a small incision as described above. Additionally, the improved implant is completely disposed within a toe of a patient, which prevents the implant from being caught on bed sheets or other objects like the conventional pins.

According to an aspect of the present disclosure, the implant can be preloaded into an adapter and provided as an implant kit. Various embodiments of such an implant kit will be described below.

Figure 30:
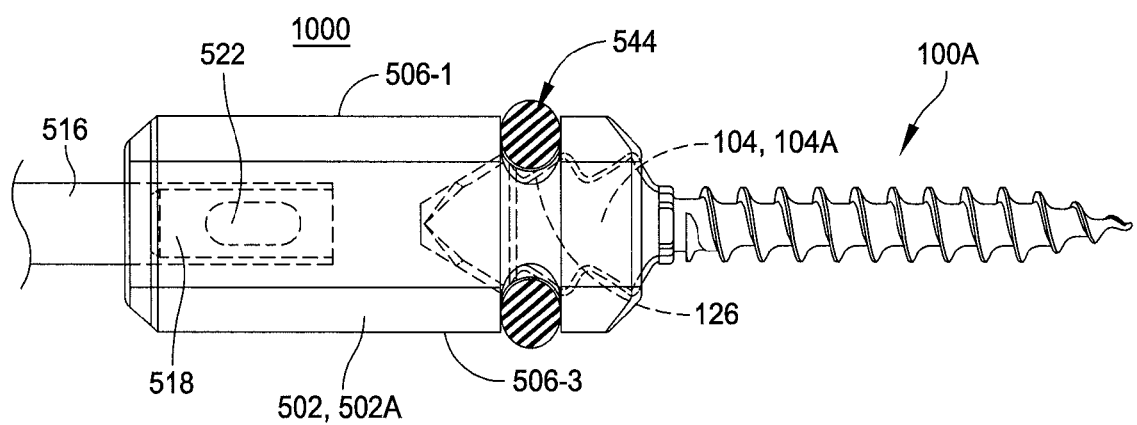
FIG. 30 illustrates an implant kit comprising a hammer toe implant preloaded in the adapter shown in FIGS. 19-22.

FIG. 30 is a view of the implant kit 1000 in which the implant 100, 100A is preloaded into the adapter 502. FIG. 30 is viewed from within the plane of FIGS. 28A and 28B so that the view shows the full circumference of the blade portion 104, 104A. In this view of FIG. 30, with the blade portion 104, 104A fully inserted into the adapter 502, 502A, an elastic O-ring 544 (also shown in FIGS. 17 and 18) placed in the groove 510 retains the implant 100, 100A in the adapter 502, 502A by preventing the implant from sliding out of the adapter. The cross-sections of the O-ring is shown in FIG. 30. The groove 510 is cut into the adapter with a sufficient depth so that when the O-ring 544 is placed therein the O-ring is positioned within the valley 126 between two adjacent teeth portions 114 about the circumference of the blade portion 104, 104A, as shown in FIG. 30. Because the O-ring 544 is elastic, one can push the blade portion 104, 104A of the implant into the adapter with sufficient force for one or more of the teeth portions 114 to push past the O-ring 544 when assembling the implant kit 1000. Once the implant kit 1000 is assembled, however, the O-ring 544 secures and retains the implant 100, 100A in the adapter 502 until one intentionally pulls off the adapter 502 after the implant is driven into a bone.

Figure 31A:
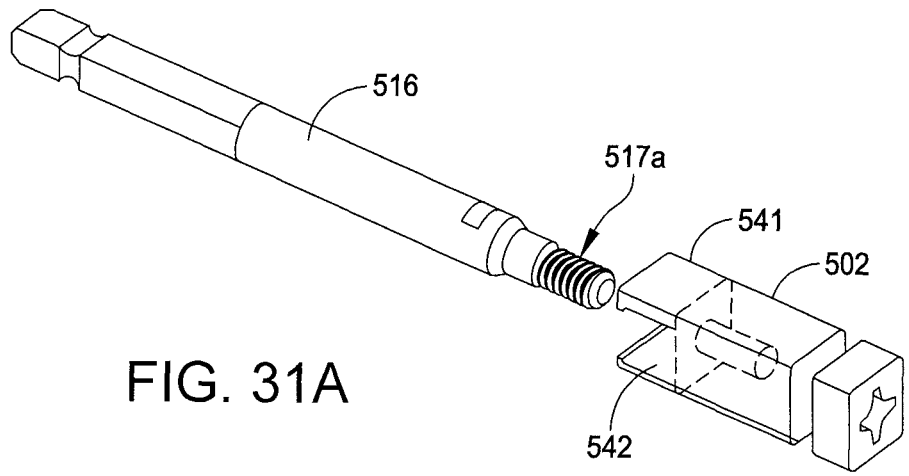
FIG. 31A is an isometric view of an implant kit according to some embodiments whose adapter has an implant receiving end configured to couple to an implant by an O-ring according to the adapter of FIGS. 19, 28A and 28B and having a driver shaft coupling end configured for coupling to the driver shaft by mating male and female threads.
Figure 31B:
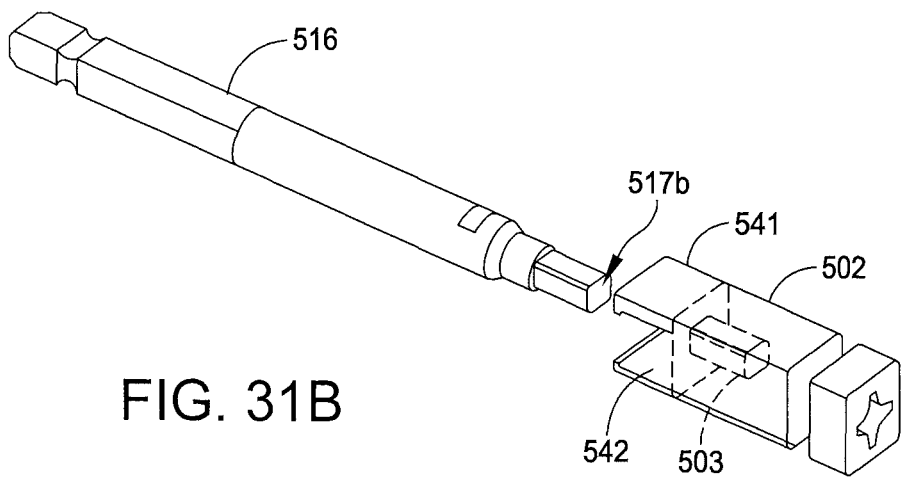
FIG. 31B is an isometric view of an implant kit according to some embodiments whose adapter has an implant receiving end configured to couple to an implant by an O-ring according to the adapter of FIGS. 19, 28A and 28B and having a driver shaft coupling end configured for coupling to the driver shaft by a pair of opposing tabs.

In use, the surgeon would attach the implant kit 1000 to the driver tool 500 to manually drive the threaded portion 102 of the implant 100, 100A into the resected surface of proximal phalange 302 as illustrated in FIG. 29. The implant 100, 100A is driven into the proximal phalange 302 until engagement portion 106 abuts the proximal phalange 302. The implant 100, 100A is then decoupled from the adapter 502 by axially pulling the adapter 502 away from the implant 100, 100A with sufficient force to push the O-ring 544 outward and separate the adapter 502 from the implant 100, 100A. Referring to FIGS. 31A through 35F, various embodiments for removably coupling the implant kits disclosed above to a driver shaft 516 of a driver tool 500 will be described. FIGS. 31A-31D are various views of some embodiments of an adapter such as the adapter 502 of FIGS. 28A, 28B, and 30 having a driver shaft coupling end configured for coupling to the adapter-engaging end 517a, 517b of the driver shaft. The driver shaft coupling end of the adapter 502 is provided with the longitudinally extending bore 514, configured for receiving the adapter-engaging end 517a, 517b, and a pair of opposing tabs 541, 542 extending longitudinally in the direction away from the implant engaging end. FIG. 31A shows a driver shaft 516 whose adapter-engaging end 517a is configured with screw threads. In this embodiment, the driver-engaging end of the adapter 502 is configured to threadably couple to the adapter-engaging end 517a of the driver shaft 502 and the tabs 541, 542 provide additional locking mechanism. FIG. 31B shows a driver shaft 516 whose adapter-engaging end 517b is configured with a magnetic tip. In this embodiment, the driver-engaging end of the adapter 502 is configured to magnetically couple to the adapter-engaging end 517b and the tabs 541, 542 provide additional locking mechanism. The adapter 502 would then be provided with a magnet or a piece of magnetic material 503 for magnetically coupling to the adapter-engaging end 517b.

Figure 31C:
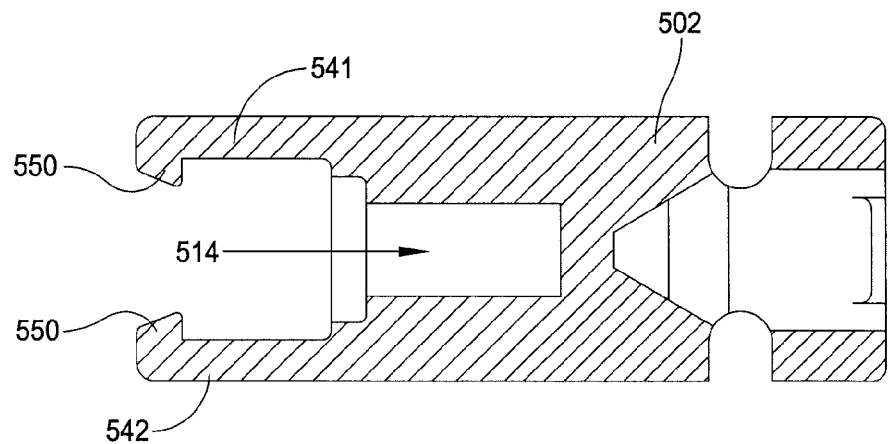
FIG. 31C is a cross-sectional view of an adapter having a driver shaft coupling end illustrated in FIG. 31B and an implant receiving end according to some embodiments.
Figure 31D:
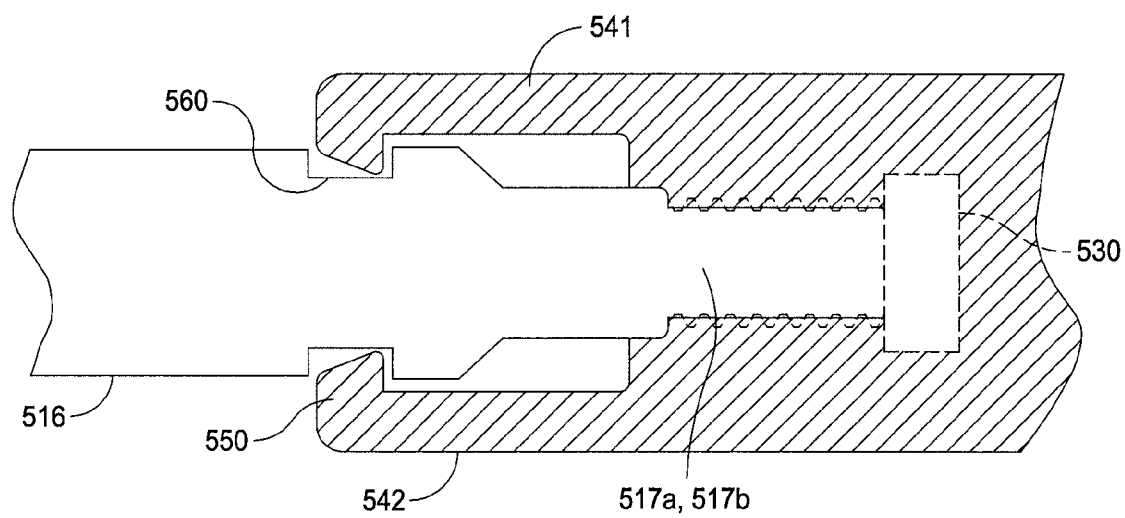
FIG. 31D is a cross-sectional view of an adapter having a driver shaft coupling end illustrated in FIG. 31A according to some embodiments.

FIGS. 31C and 31D are cross-sectional views of the adapter 502 showing the driver-engaging end. FIG. 31C shows the profile of the tabs 541 and 542 and the bore 514 for receiving the adapter-engaging end 517 of the driver shaft. If the adapter 502 is intended for use with the driver shaft 516 of the embodiment shown in FIG. 31A, the bore 514 is tapped with screw thread for threadably engaging the threaded adapter-engaging end 517a. If the adapter 502 is intended for use with the driver shaft 516 of the embodiment shown in FIG. 31B, the bore 514 is provided with a magnet 530 for engaging the magnetized tip of the adapter-engaging end 517b.

The tabs 541, 542 and the adapter-engaging end 517a, 517b are configured for further mechanical coupling. In the illustrated example, the tabs 541, 542 are provided with bumps 550 and the adapter-engaging end 517a, 517b of the driver shaft is provided with corresponding cutouts 560 for mating with the bumps 550.

Figure 32A:
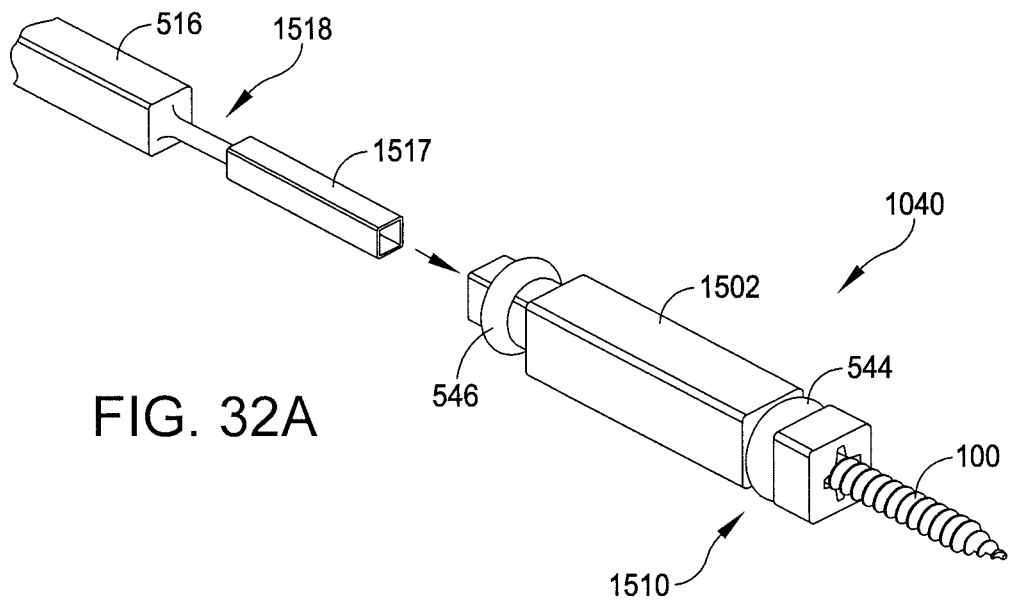
FIG. 32A is an isometric view of an implant kit according to some embodiments whose adapter has an implant receiving end configured to couple to an implant by an O-ring according to the adapter of FIGS. 19, 28A and 28B and having a driver shaft coupling end configured for coupling to the driver shaft by an O-ring.
Figure 32B:
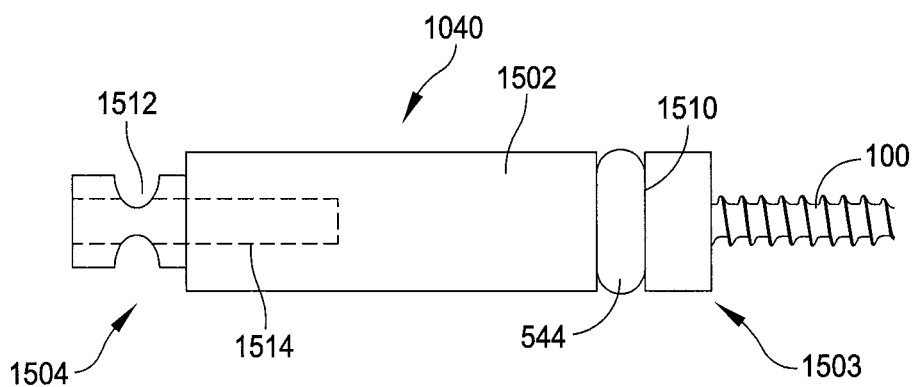
FIG. 32B is a side view of an adapter has an implant receiving end configured to couple to an implant by an O-ring according to the adapter of FIGS. 19, 28A and 28B and having a driver shaft coupling end configured for coupling to the driver shaft by an O-ring according to some embodiments.
Figure 32C:
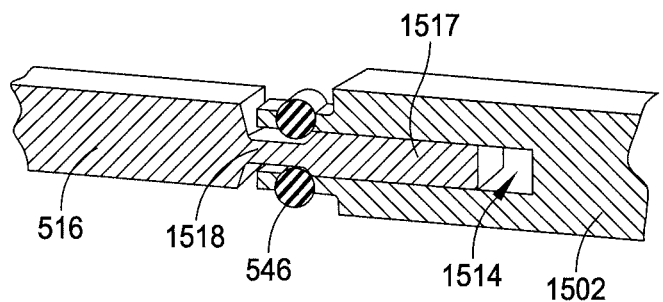
FIG. 32C is a cross-sectional view of an implant kit whose adapter has a driver shaft coupling end for coupling to the driver shaft by an O-ring according to some embodiments.

Shown in FIGS. 32A-32C are various views of an implant kit 1040 comprising an adapter 1502 and an implant 100 according to some embodiments. The implant 100 is removably coupled to the adapter 1502 at the adapter's implant-receiving end 1503 by a first O-ring 544 in the same manner as with the adapter 502 shown in FIGS. 19, 28A, 28B and 30. The adapter 1502 has a circumferential groove 1510, in which the first O-ring 544 is provided, in the outer surface of the adapter in proximity to the implant-receiving end 1503. As with the adapter embodiment 502, the adapter 1502 comprises a slot provided in the implant-receiving end 1503 that receives the blade portion 104 of the implant 100. The adapter 1502 also has a driver shaft coupling end 1504 configured for removably coupling to the driver shaft 516 by a second O-ring 546. The driver shaft coupling end 1504 is provided with a longitudinally extending bore 1514 for receiving the adapter-engaging end 1517 of the driver shaft 516. The driver shaft coupling end 1504 is also provided with a second circumferential groove 1512 in which the second O-ring 546 is disposed. The adapter-engaging end 1517 has a cross-section that is larger than the inner diameter of the second O-ring 546 but has a turned down section 1518 that has a reduced cross-section for accommodating the second O-ring 546 when the adapter-engaging end 1517 is inserted into the bore 1514 as shown in FIG. 32C. When the adapter-engaging end 1517 is inserted into the bore 1514, the turned down section 1518 and the second circumferential groove 1512 align so that the second O-ring 546 rests in the turned down section 1518. The second O-ring 546 thus provides an interference with the adapter-engaging end 1517 to prevent the adapter 1502 and the driver shaft 516 from decoupling without exerting some force.

Figure 33A:
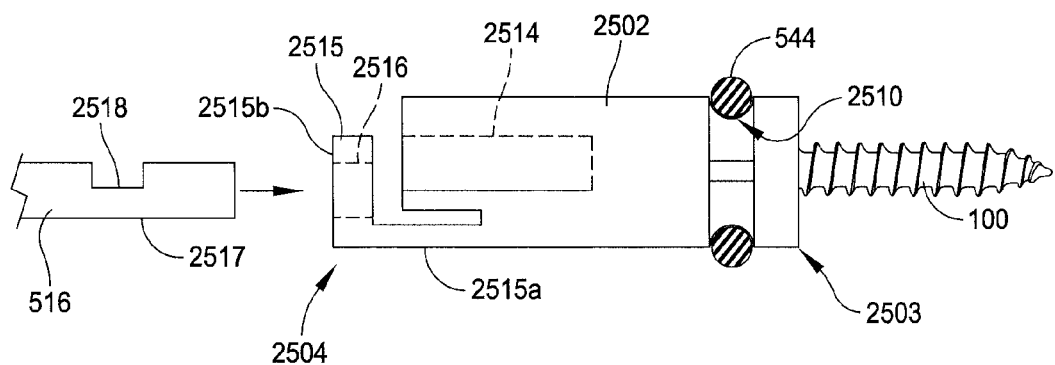
FIG. 33A is a side view of an implant kit according to some embodiments whose adapter has an implant receiving end configured to couple to an implant by an O-ring according to the adapter of FIGS. 19, 28A and 28B and having a driver shaft coupling end configured for coupling to the driver shaft by an off-set clip.
Figure 33B:
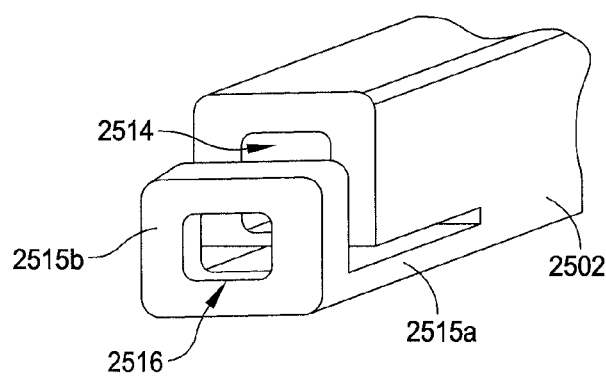
FIG. 33B is an end perspective view of an adapter having a driver shaft coupling end configured for coupling to the driver shaft by an off-set clip according to some embodiments.
Figure 33C:
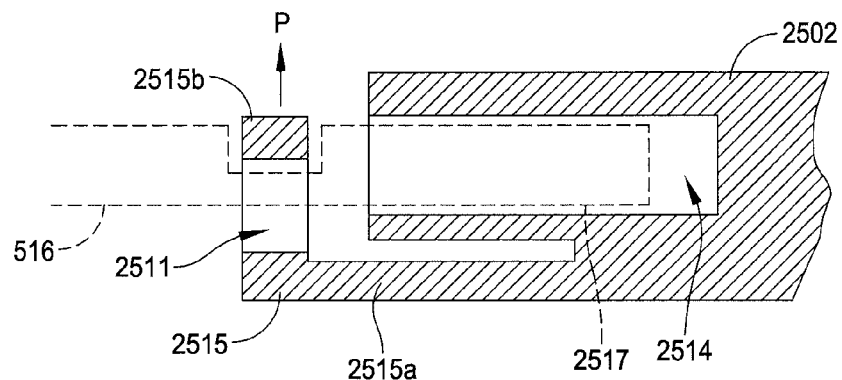
FIG. 33C is a cross-sectional view of an adapter having a driver shaft coupling end configured for coupling to the driver shaft by an off-set clip according to some embodiments.

FIGS. 33A-33C are various views of an adapter 2502 that can be used in an implant kit 1050 according to some embodiments of the present disclosure. The adapter 2502 has an implant receiving end 2503 configured to couple to an implant 100 by an O-ring 544 according to the adapter of FIGS. 19, 28A and 28B and a driver shaft coupling end 2504 configured for coupling to the driver shaft 516 by an off-set clip 2515. The driver shaft coupling end 2504 has a longitudinally extending bore 2514 for receiving an adapter-engaging end 2517 of the driver shaft 516. The off-set clip 2515 is cantilevered to the adapter having a cantilever portion 2515a connected to the adapter body and a locking portion 2515b extending orthogonal to the cantilever portion 2515a. The locking portion 2515b is provided with a through hole 2516 for the adapter-engaging end 2517 of the driver shaft 516. The through hole 2516 and the bore 2514 are off-set to enable the locking function. The adapter-engaging end 2517 is provided with a groove or a cutout 2518 on one side for removably engaging the off-set clip 2515. To insert the adapter-engaging end 2517 into the adapter, the user pushes the off-set clip 2515 in the direction shown by the arrow P in FIG. 33C, which is a longitudinal cross-sectional view of the adapter 2502. That will deflect the cantilever portion 2515a in the direction P and bring the through hole 2516 in linear alignment with the bore 2514 so that the adapter-engaging end 2517 can be inserted through the through hole 2516 and the bore 2514. Once the adapter-engaging end 2517 is fully inserted, the off-set clip 2515 is released to its normal off-set position as shown in FIG. 40C. The off-set position of the locking portion 2515b keeps the locking portion 2515b seated within the cutout 2518 keeping the driver shaft 516 coupled to the adapter 2502. The off-set clip can be configured so that in the configuration shown in FIG. 33C, the locking portion 2515b maintains a force against the cutout 2518 in the direction opposite the arrow P. To remove the adapter 2502 from the adapter-engaging end 2517, the off-set clip 2515 is pushed in the direction of the arrow P shown in FIG. 33C bringing the through hole 2516 and the bore 2514 into longitudinal alignment and thus removing the interference between the locking portion 2515b and the cutout 2518. In some embodiments, the adapter-engaging end 2517 may simply be straight without the cutout 2518 structure. In that embodiment, the urging of the locking portion 2515b against the straight adapter-engaging end 2517 in the direction opposite the arrow P will provide sufficient frictional interference to keep the driver shaft 516 and the adapter 2502 coupled.

Figure 34A:
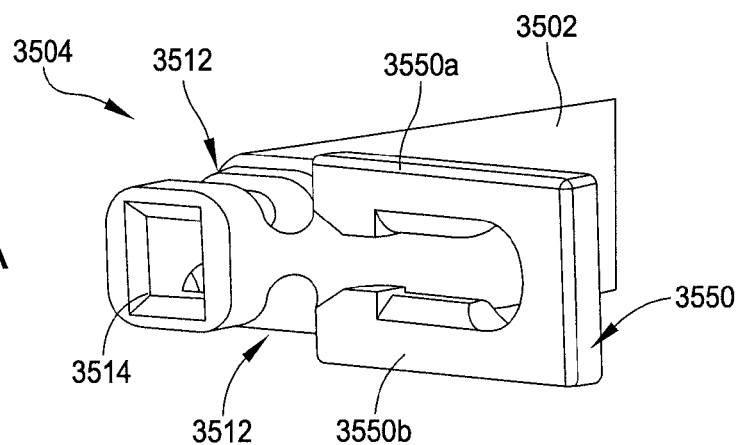
FIG. 34A is an end perspective view of an adapter having a driver shaft coupling end configured for coupling to the driver shaft by a C-clip according to some embodiments.
Figure 34B:
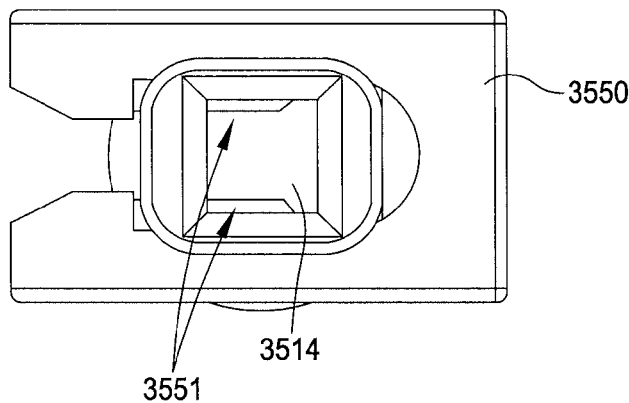
FIG. 34B is an end view of an adapter having a driver shaft coupling end configured for coupling to the driver shaft by a C-clip according to some embodiments.
Figure 34C:
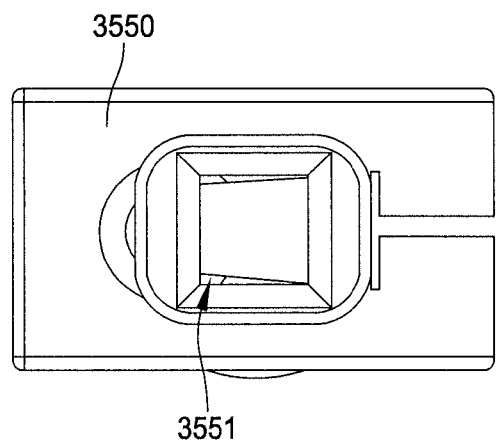
FIG. 34C is an end view of an adapter having a driver shaft coupling end configured for coupling to the driver shaft by a C-clip according to some embodiments.
Figure 34E:
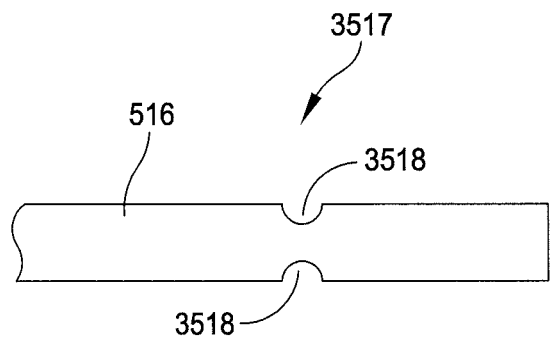
FIG. 34E is a side view of a driver shaft configured for coupling to a driver shaft-coupling end of the adapter illustrated in FIG. 34D according to some embodiments.
Figure 34D:
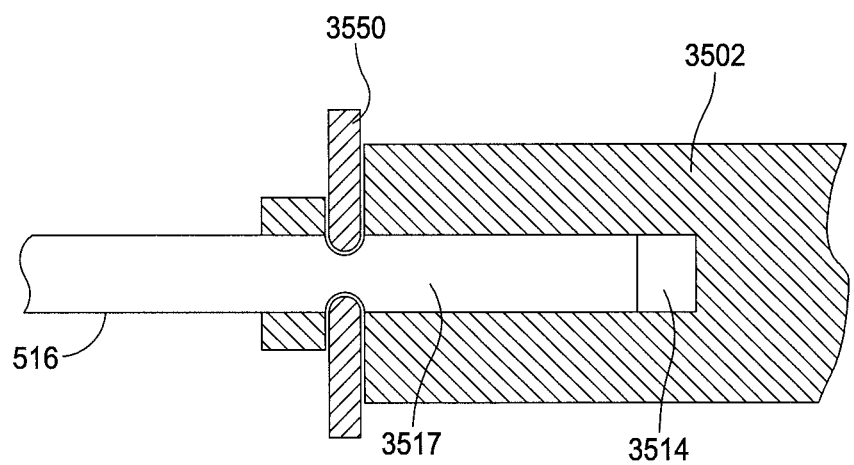
FIG. 34D is cross-sectional view of an implant kit according to some embodiments having a driver shaft coupling end configured for coupling to the driver shaft by a C-clip.

FIGS. 34A-34E are various views of the driver shaft coupling end 3504 of an adapter 3502 that is configured for removably coupling to the implant 100 to form an implant kit according to some embodiments. The implant-receiving end of the adapter 3502 is configured to couple to the implant by an O-ring 544 according to the adapter of FIGS. 19, 28A and 28B. The driver shaft coupling end 3504 is configured to removably couple to the adapter-engaging end 3517 of the driver shaft 516 by a C-clip 3550. The C-clip 3550 is generally shaped like a letter C and has two prongs 3550a and 3550b joined at one end and open at the opposite end. The driver shaft coupling end 3504 of the adapter 3502 is provided with a bore 3514 for receiving the adapter-engaging end 3517. The driver shaft coupling end 3504 is further configured with a pair of slots 3512 for receiving the C-clip 3550 and oriented orthogonal to the longitudinal axis of the adapter 3502. FIG. 34B is an end view of the adapter assembly viewed from the driver shaft coupling end 3504 showing the C-clip 3550 clipped on to the adapter 3502 by sliding the two prongs 3550a, 3550b into the pair of slots 3512. The pair of slots 3512 are cut into the adapter 3502 sufficiently deep to overlap with the bore 3514 so that when the C-clip 3550 is clipped on to the adapter 3502, interference tabs 3551 on each of the two prongs 3550a, 3550b protrude into the bore 3514 as shown in FIG. 34B. When the adapter-engaging end 3517 of the driver shaft 516 is inserted into the bore 3514 and locked with the C-clip 3550 as shown in the longitudinal cross-sectional view of FIG. 34E, the interference tabs 3551 reside in the corresponding slots 3518 provided in the adapter-engaging end 3517 and prevent the adapter 3502 and the driver shaft 516 from decoupling. In this embodiment, the interference tabs 3551 are oriented substantially parallel to one another. In one preferred embodiment, the interference tabs 3551 can be oriented in a slant so that the interference tabs 3551 are tapered towards the open end of the C-clip 3550. The tapered interference tabs 3551 makes is easier to insert the C-clip 3550 over the adapter-engaging end 3517.

Figure 35A:
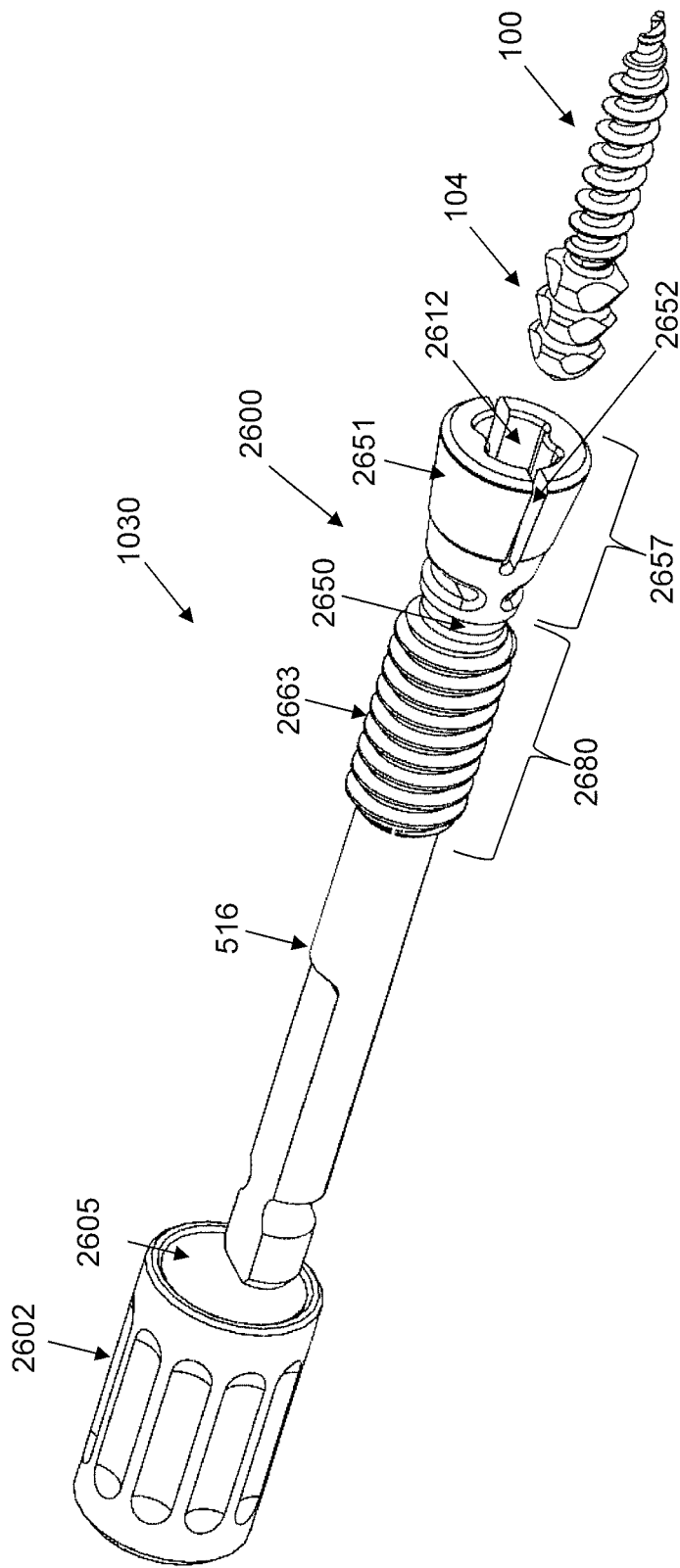
FIG. 35A is an isometric view of some embodiments of an implant kit comprising an adapter that is configured for coupling to an hammer toe implant using a collet.

FIGS. 35A-35F are various views of some embodiments of an implant kit 1030 comprising an adapter 2600 configured for coupling to a hammer toe implant 100 using a thread-biased collet 2650. The adapter 2600 comprises a sleeve 2602 and the collet 2650. The sleeve 2602 has openings at each end and a bore 2615 longitudinally extending between the two openings. As shown in FIGS. 35A and 35B, sleeve 2602 can include a plurality of ribs that extend in a longitudinal direction along sleeve 2602 to provide a gripping surface for a user. The collet 2650 is received in the bore 2615. The sleeve 2602 has a first end 2605 that forms one of the openings.

Figure 35C:
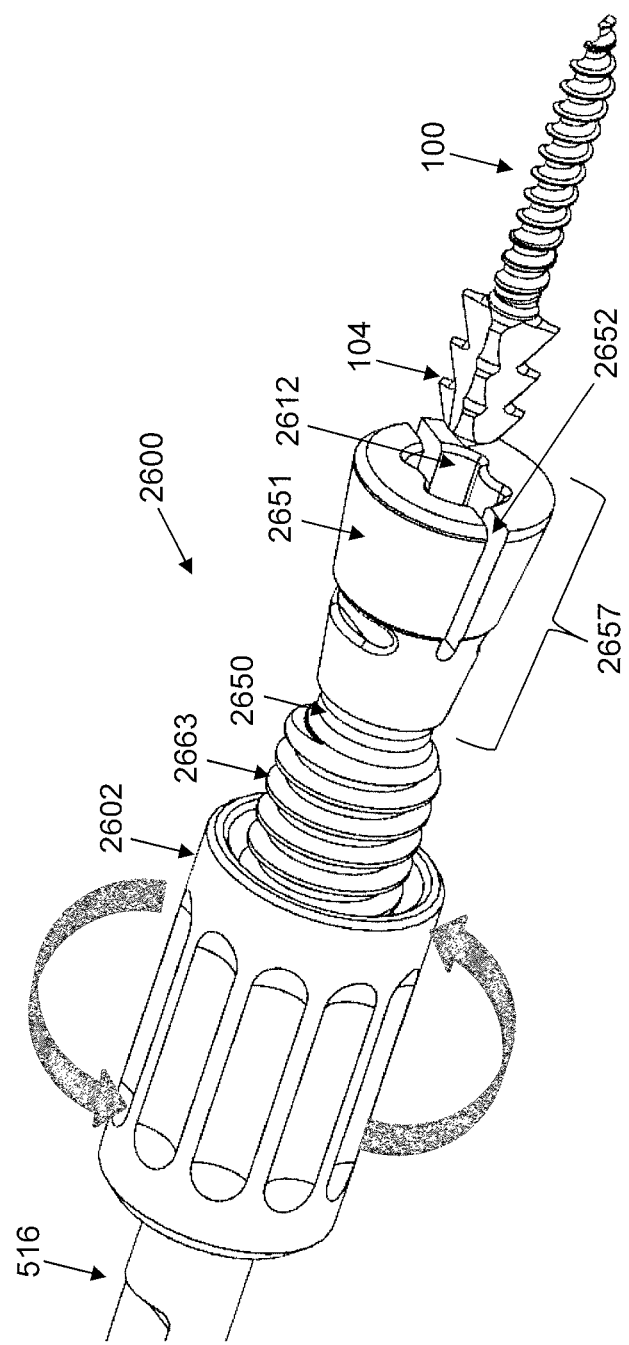
FIG. 35C is an isometric view of some embodiments of an implant kit comprising an adapter that is configured for coupling to an hammer toe implant using a collet.

Referring to FIG. 35A, the collet 2650 is generally cylindrical in shape and comprises an implant receiving portion 2657 and a threaded portion 2660. The threaded portion 2660 is provided with screw threads 2663. The implant receiving portion 2657 has an implant-receiving opening 2612 for receiving the blade portion 104 of the implant 100. The implant-receiving opening 2612 is defined by collet segments 2651 which are defined by slots 2652 extending from the implant-receiving end towards the threaded portion 2660. This example of a collet has two collet segments 2651. The implant receiving portion 2657 is flared in its outer circumference so that the diameter of the receiving portion 2657 increases towards the implant-receiving end of the collet. FIG. 35B shows the collet 2650 with the implant 100 received in the slots 2652. FIG. 35C shows the collet with an indicated direction of rotation L to drive the sleeve 2602 onto the threaded portion 2660 to retain the implant 100 within implant receiving portion 2657. In various embodiments, the refraction and extension of the collet 2650 is enabled by turning the sleeve 2602 about a longitudinal axis relative to the collet 2650 thus engaging the screw threads 2607 and 2663. In some embodiments, sleeve 2602 is driven by hand in direction of rotation L to retain implant 100 within implant receiving portion 2657 pre-implantation and in an opposite direction of L to release implant 100 post-implantation.

FIG. 35D is an end view of the adapter 2600 illustrated in FIGS. 35A-35C and shows the implant 100 received in the implant receiving end 2657 and slots 2652. The implant-receiving opening 2612 of implant receiving portion 2657 has a geometry that complements the cross-sectional geometry of blade portion 104 of implant 100 and is defined by collet segments 2651 which are defined by slots 2652. For example, if implant 100 has a cylindrical, cruciform straight blade portion 104 as illustrated in FIG. 2 and FIG. 35A, then implant-receiving opening 2612 can extend approximately parallel to the lengthwise direction of collet 2650. If the blade portion 104 of implant 100 is angled (not shown), then implant-receiving opening 2612 can extend from end 2603 at an angle relative to the plane defined by collet 2650 as will be understood by one skilled in the art. In various embodiments, as shown in FIGS. 35A and 35D, collet segments 2651 of implant receiving end 2657 include radii features to complement radii features of the cylindrical, cruciform blade portion 104.

Figure 35F:
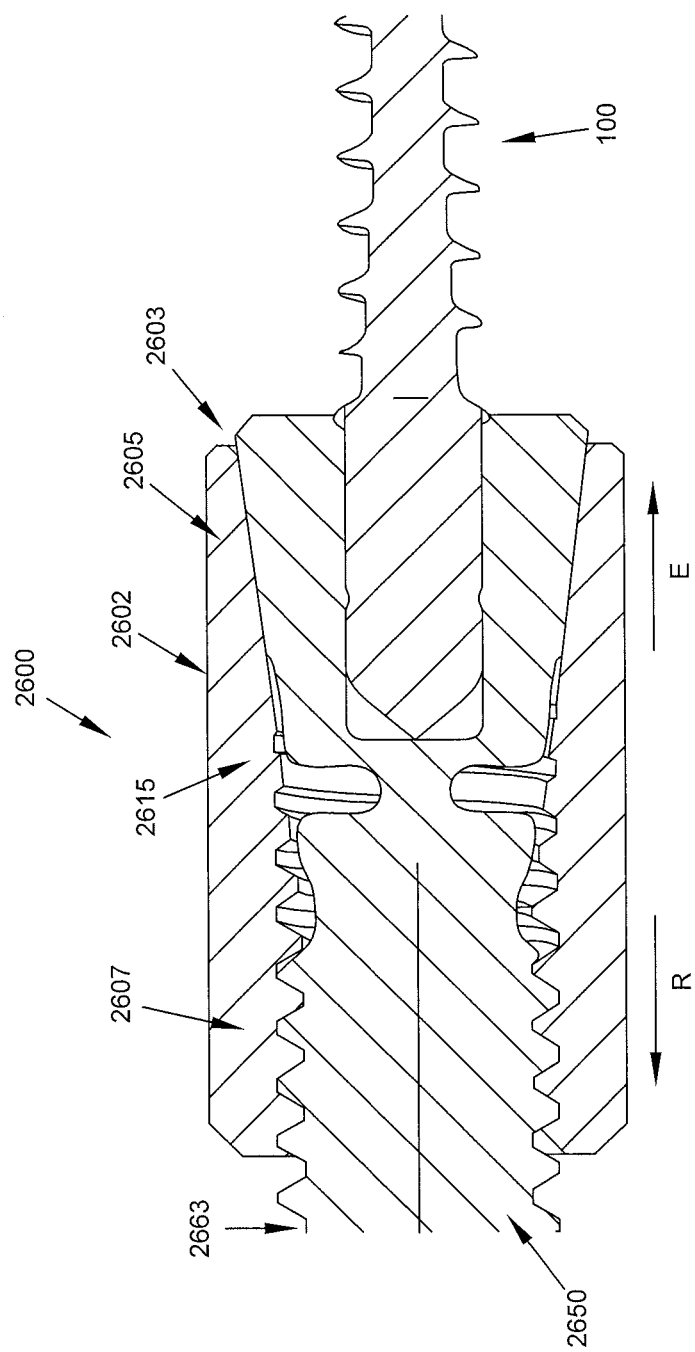
FIG. 35F is cross-sectional view of the implant kit taken along line 25-25 in FIG. 35D.

Referring now to FIGS. 35E and 35F, the bore 2615 has a screw threaded portion 2607 and a main portion 2605. The threaded portion 2607 is configured to threadably engage the threads 2663 of the collet 2650. The main portion 2605 has a sufficiently large diameter to accommodate a substantial portion of the implant receiving portion 2657 of the collet 2650 without imposing any mechanical interference. The main portion 2605 terminates at the first end 2603 where the opening formed therein has a diameter smaller than the maximum diameter of the flared implant receiving portion 2657. This configuration allows the collet segments 2651 to be constricted by the first end 2603 when the collet 2650 is retracted into the sleeve 2602 in the direction R shown in FIG. 35F and close in on the blade portion 104 of the implant 100, thus, retaining the implant. Conversely, the implant 100 can be released from the adapter 2600 by extending the collet 2650 outward from the sleeve 2602 in the direction E shown in FIG. 35F. In some embodiments, and as shown in FIG. 35F, sleeve 2602 includes an internal taper to interface with an external taper of the implant receiving portion 2657 of collet 2650.

Figure 36A:
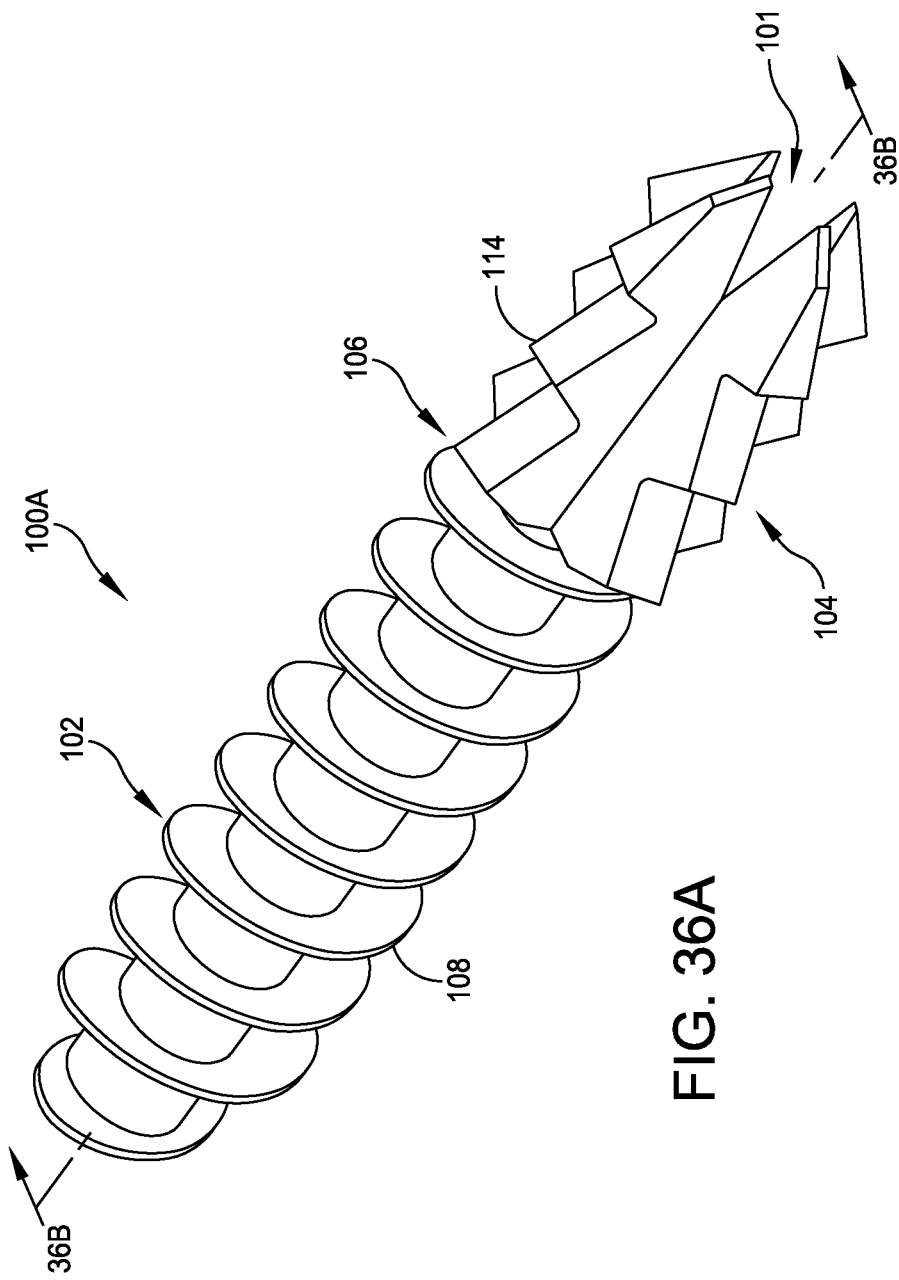
FIG. 36A is an isometric view of another example of hammer toe implant according to some embodiments.
Figure 36B:
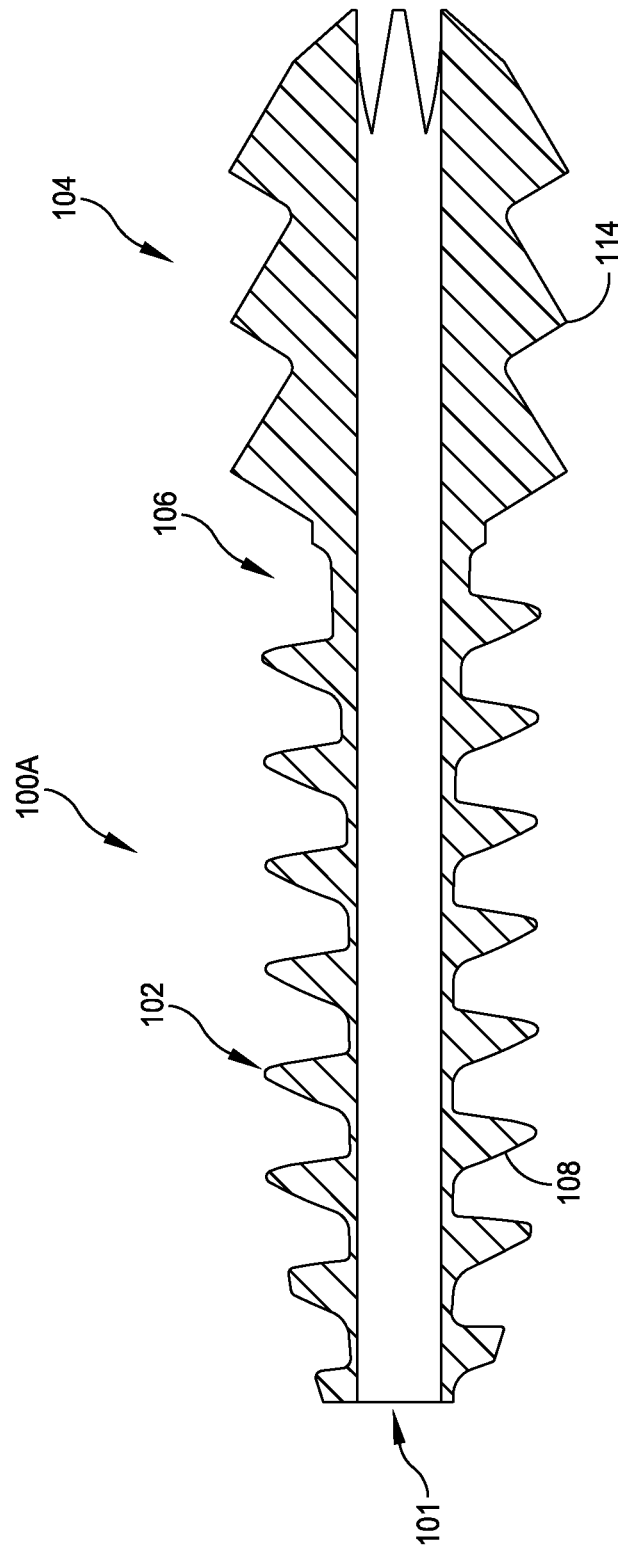
FIG. 36B is a top side view of the hammer toe implant illustrated in FIG. 36A.

FIGS. 36A and 36B illustrate one example of an implant 100A that can be used with the two-wire insertion technique described herein. Implant 100A is identified to implant 100 except that implant 100A includes a central passageway 101 that extends through the entire length of implant 100A. Descriptions of the features of implant 100A that are identical to the features of implant 100 are not repeated.

Figure 37:
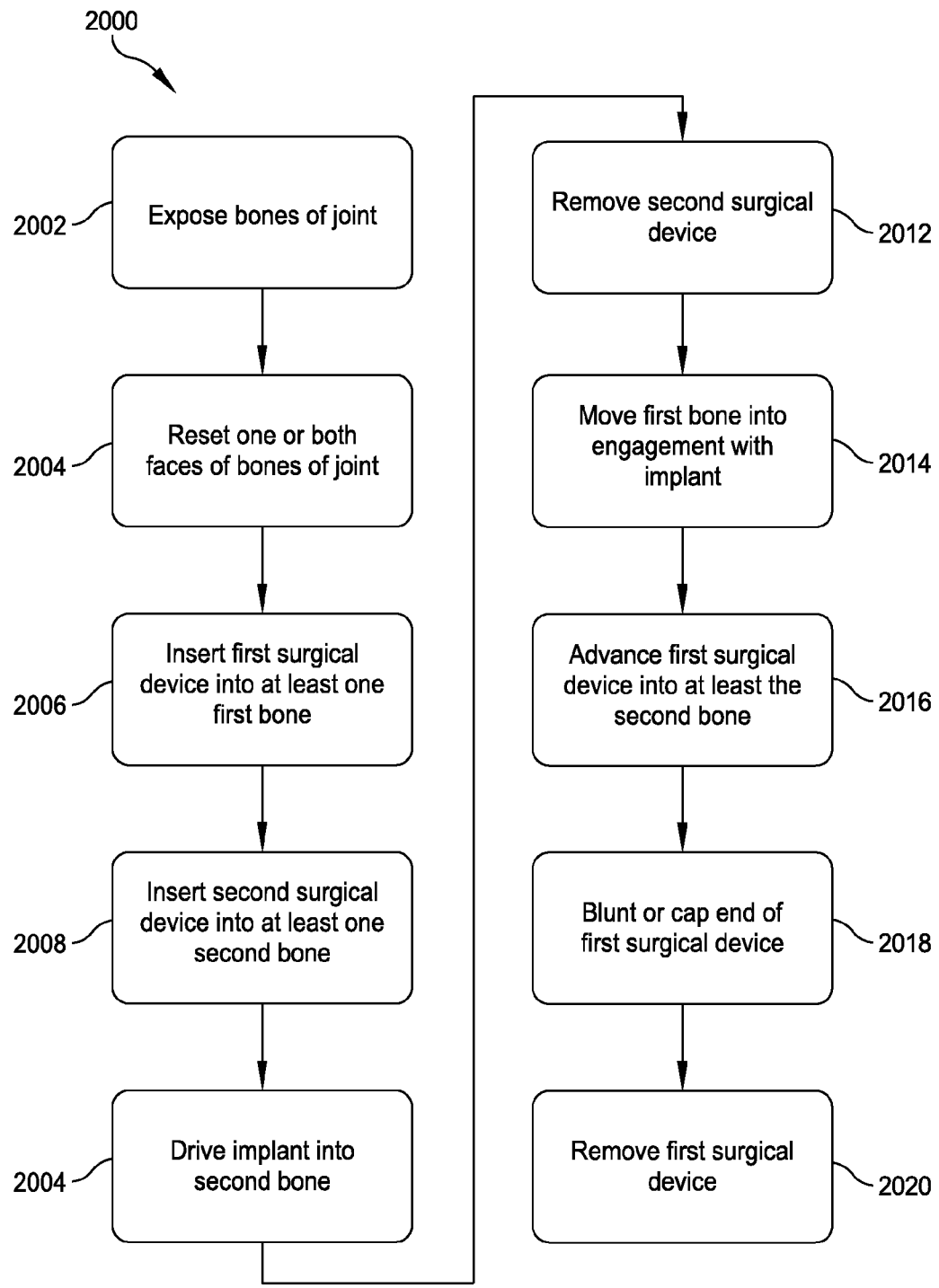
FIG. 37 is a flow diagram of one example of method of installing an implant in accordance with some embodiments.

FIG. 37 is a flow diagram of one example of installing a hammer toe implant using a two-wire technique in accordance with some embodiments. Method 2000 depicted in FIG. 37 is described with reference to FIGS. 38-45, which illustrate various steps of installing a hammer toe implant. Although the following descriptions are provided with respect to installing implant 100A, it will be appreciated that implants having other shapes and configurations can be used so long as they include a passageway for accommodating a k-wire as will be apparent after reading the following description. One example of such an alternative implant is disclosed in commonly assigned U.S. patent application Ser. No. 14/043,105, filed Oct. 1, 2013 and entitled "Hammer Toe Implant and Method," the entirety of which is incorporated by reference herein. As will be appreciated by one of ordinary skill in the art, the implants can have other fixation features. For example, both ends of the implant can have blades instead of one blade portion and one threaded portion. In some embodiments, the implant can include a blade or threaded portion at one end and an expanding portion (e.g., divergent legs or arms) at the opposite end.

Further, although method 2000 is described as installing an implant in the bones of a proximal interphelangeal joint (PIP) 300, i.e., the joint between proximal phalange 302 and middle phalange 304, one of ordinary skill in the art will understand that the technique may be applied to other joints, such as, for example, the distal interphelangeal (DIP) joint, i.e., joint 308 between middle phalange 304 and distal phalange 306.

Figure 38:
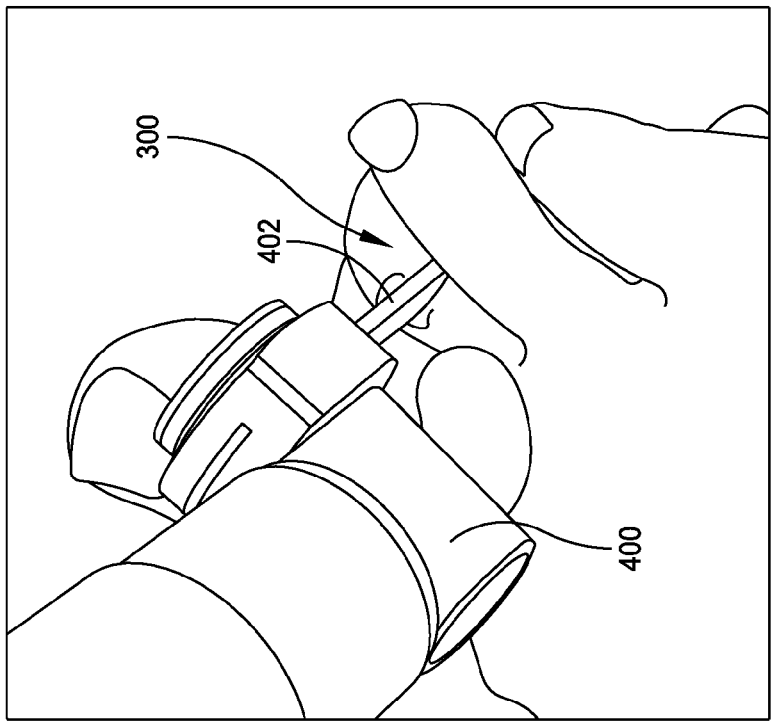
FIG. 38 illustrates a joint being accessed using a cutting tool in accordance with some embodiments.

At block 2002 of FIG. 37, an incision is made to expose the PIP joint 300. For example, FIG. 38 illustrates one example of the PIP joint 300 being exposed by using a cutting tool 400 having a blade 402.

Figure 39:
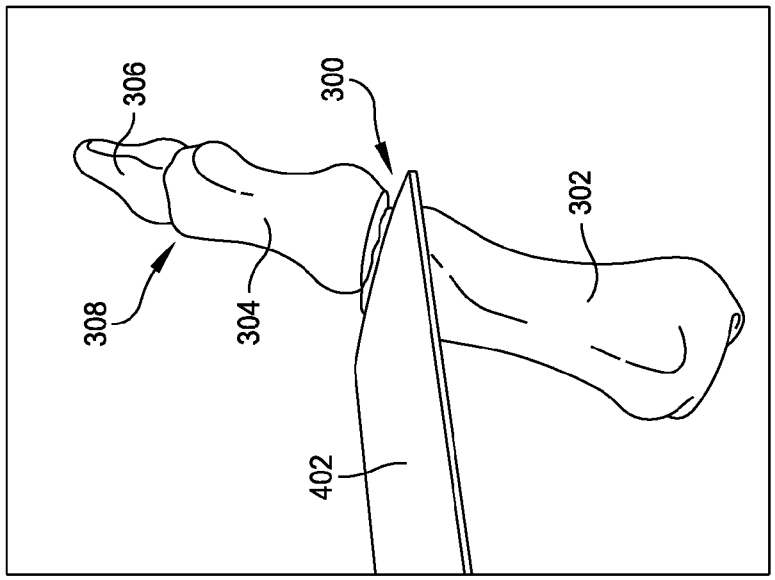
FIG. 39 illustrates the middle and proximal phalangees of a foot being resected in accordance with some embodiments.

At optional block 2004 (FIG. 37), the blade 402 of a cutting tool 400, such as a saw, is used to resect one or both of the adjacent faces of proximal phalange 302 and middle phalange 304 as illustrated in FIG. 39 The resected surfaces of proximal phalange 302 and middle phalange 304 can be debrided as understood by one skilled in the art.

Figure 40:
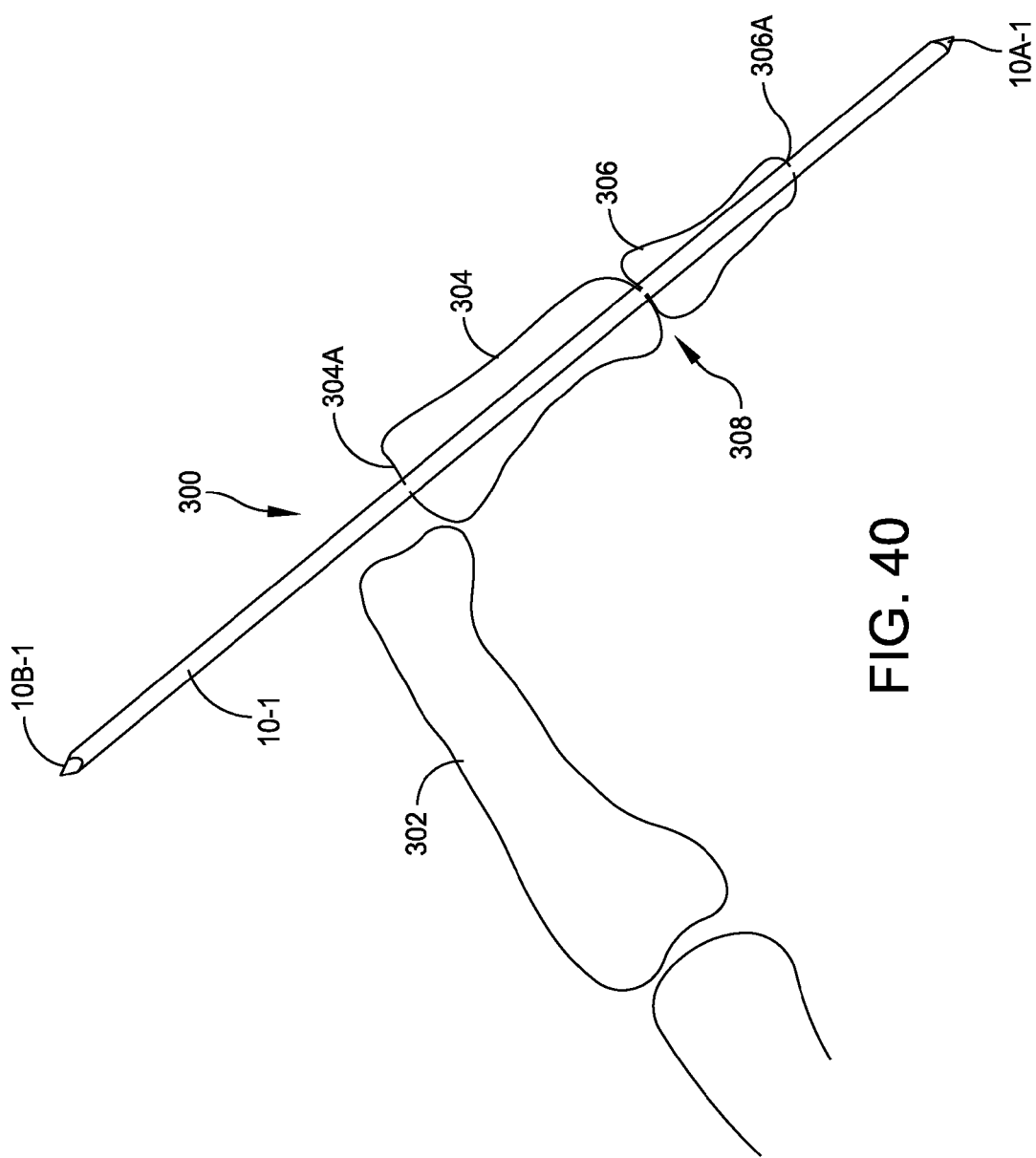
FIG. 40 illustrates a surgical device being inserted through the middle and distal phalanges in accordance with some embodiments.

At block 2006 (FIG. 37), bones are flexed apart and a first k-wire, pin, or other surgical device 10-1 is inserted into the proximal face of middle phalange 304. In some embodiments, the leading end 10A-1 of wire 10-1 is forced across the joint between middle phalange 304 and distal phalange 306, through distal phalange 306, and out the distal tip 306A of distal phalange 306 as shown in FIG. 40. The k-wire 10-1 continues to be advanced until the trailing end 10B-1 is disposed adjacent to the proximal face 304A of middle phalange 304 such that joint 300 is accessible. For example, the trailing end 10B-1 of wire 10-1 can extend slight from or be flush with the proximal face 304A of middle phalange 304. In some embodiments, trailing end 10B-1 is disposed entirely within middle phalange 304.

Figure 41:
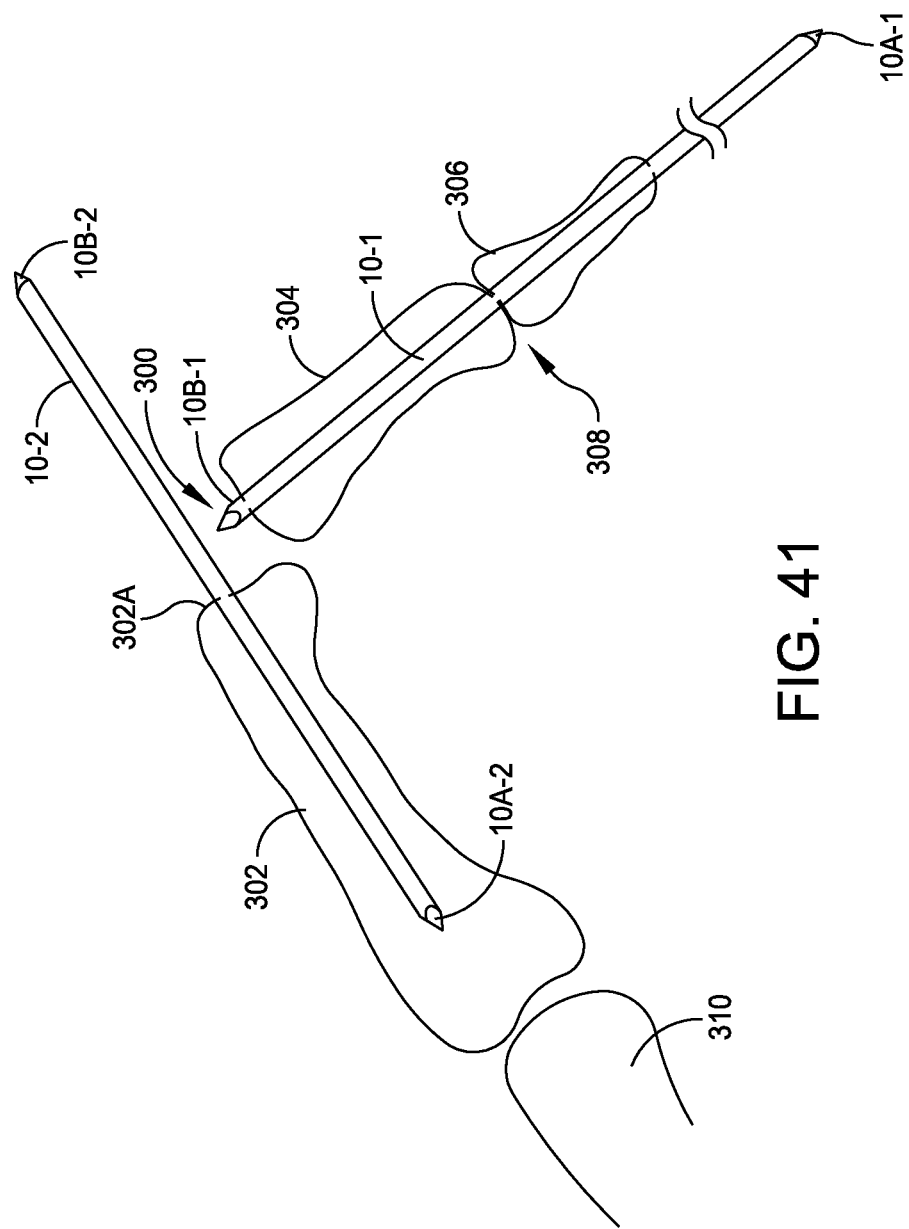
FIG. 41 illustrates a second surgical device being inserted to a proximal phalange while the first surgical device remains disposed within the middle and distal phalanges in accordance with some embodiments.

At block 2008 (FIG. 37), a second k-wire or pin 10-2 in inserted into the exposed distal face 302A of proximal phalange 302 while the first wire 10-1 is still disposed within middle phalange 304 and distal phalange 306 as shown in FIG. 41. In some embodiments, leading end 10A-2 of wire 10-2 is advanced such that it is disposed within proximal phalange 302. However, in some embodiments, leading end 10A-2 is further advanced such that it is received within metatarsal 310 and/or cuneiform (not shown).

Figure 42A:
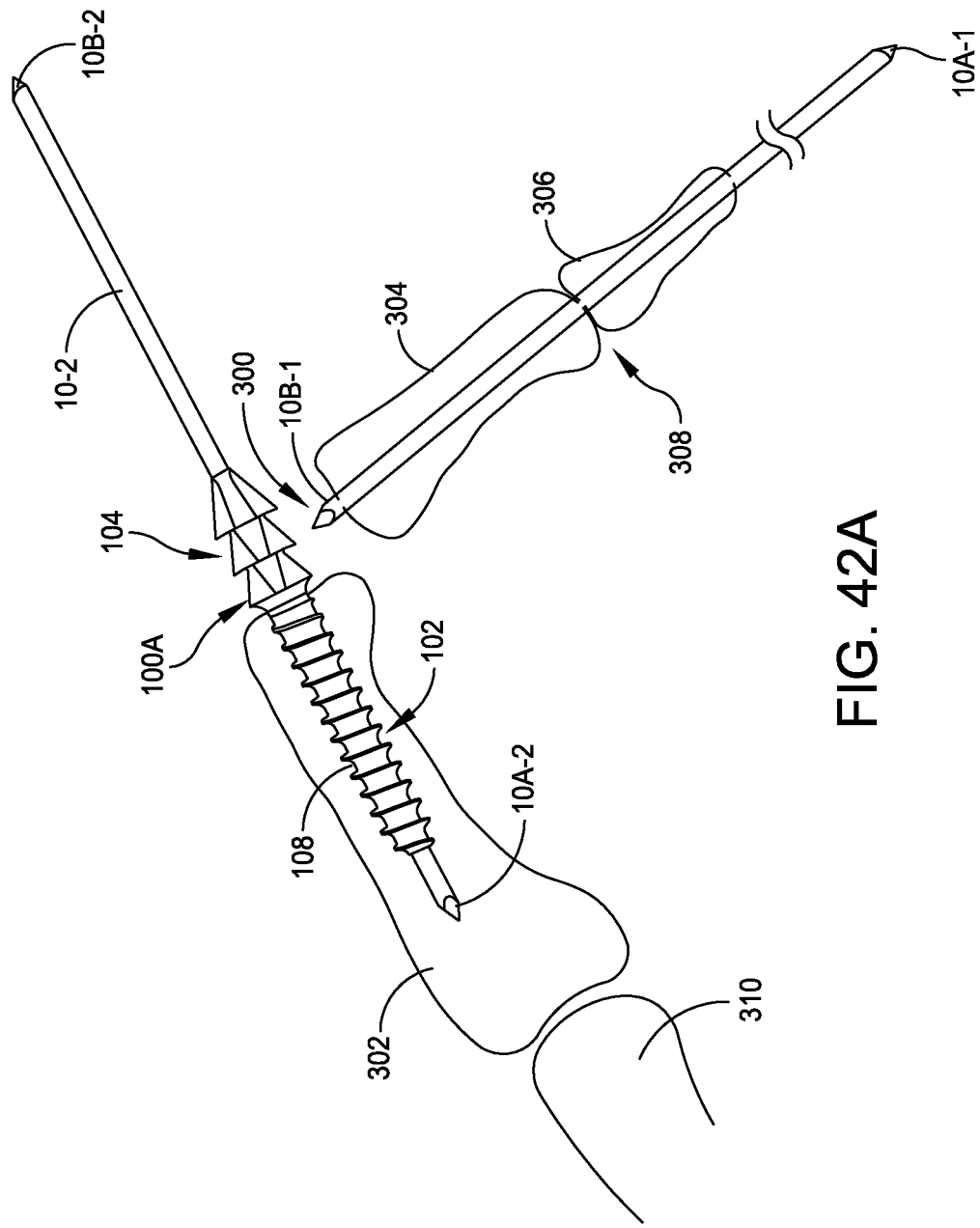
FIG. 42A illustrates an implant and surgical device being disposed within the proximal phalange while the first surgical device remains disposed within the middle and distal phalanges in accordance with some embodiments.

At block 2010 (FIG. 37), implant 100A is driven into engagement with proximal phalange 302 as shown in FIG. 42A. In some embodiments, the implant 100A is driven into proximal phalange 302 using wire 10-2 as a guide. For example, the implant 100A is slid over trailing end 10B-2 of wire 10-2 by receiving wire 10-2 within passageway 101 of implant 100A. An installation tool, such as one of driver assembly 500 and/or installation kit 1030, including adapter 2600, can be used to engage the blade portion 104 of implant 100A and drive threaded portion 102 into middle phalange 302 as implant 100A is guided by wire 10-2.

Figure 42B:
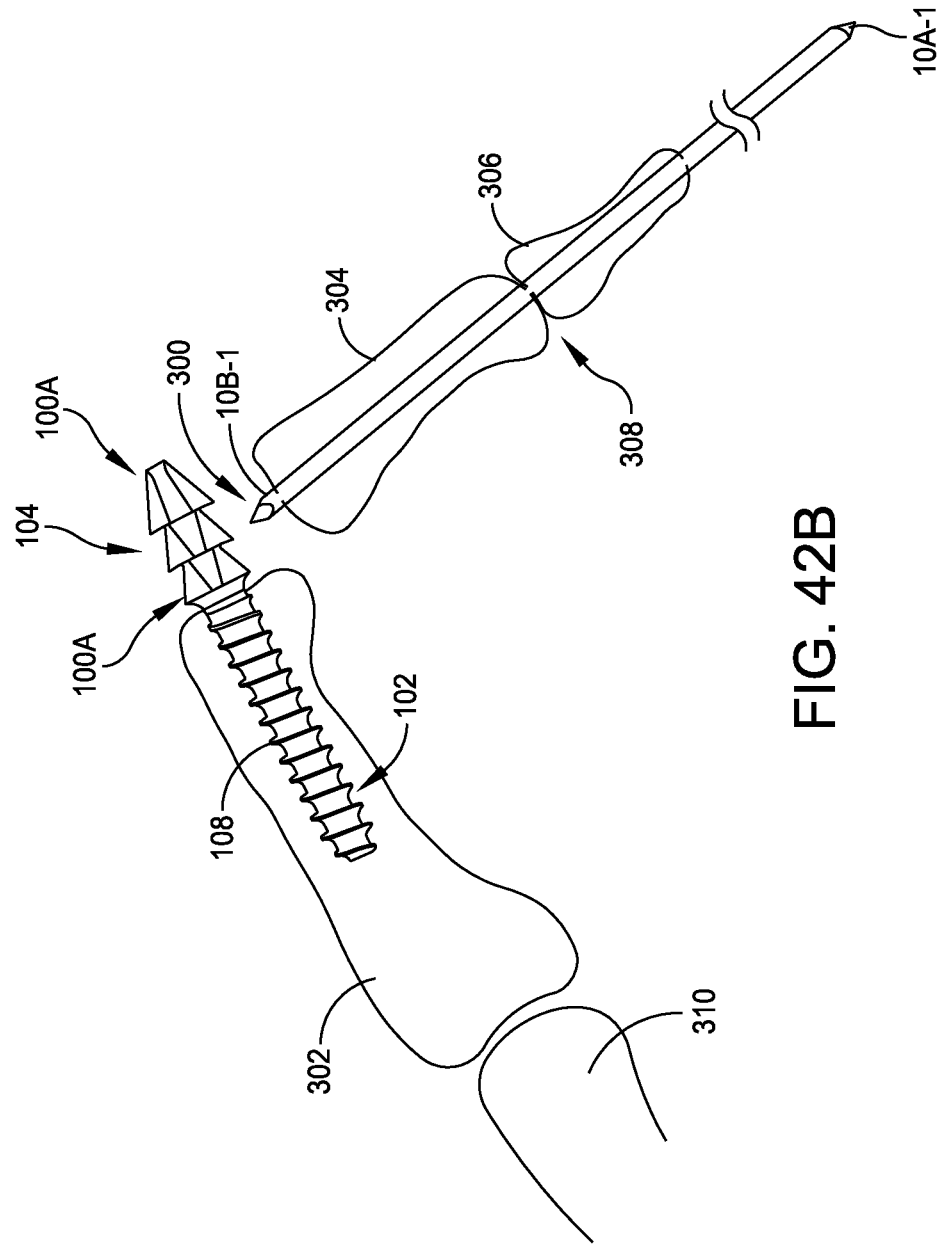
FIG. 42B illustrates the implant being disposed within the proximal phalange after the second surgical device has been removed and while the first surgical device remains disposed within the middle and distal phalanges in accordance with some embodiments.

At block 2012 (FIG. 37), second k-wire or pin 10-2 is removed from its engagement with implant 100A and proximal phalange 302 (and metatarsal 310 and cuneiform (not shown), if applicable). Implant 100A remains engaged with proximal phalange 302 once wire 10-2 has been removed as shown in FIG. 42B.

Figure 43:
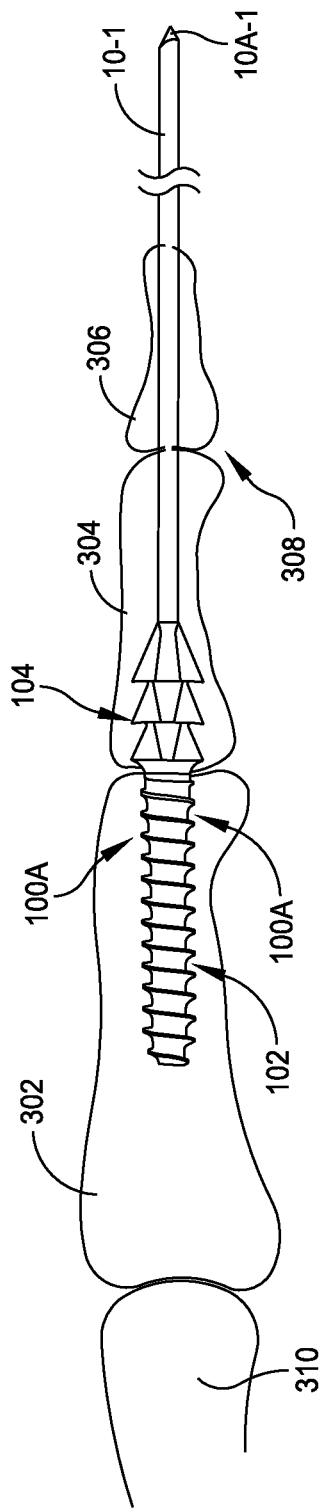
FIG. 43 illustrates the middle phalange having been pressed into engagement with the implant using the first surgical device as a guide in accordance with some embodiments.

At block 2014 (FIG. 37), the middle phalange 304 is moved into engagement with implant 100A. For example, with wire 10-1 still disposed within middle and distal phalanges 304, 306, the middle and distal phalanges 304, 306 and wire 10-1 are manipulated such that the trailing end 10B-1 of wire 10-1 is aligned with the passageway 101 of implant 100A. In some embodiments, wire 10-1 can be inserted into passageway 101 prior to the middle phalange 304 being forced into engagement with the blade portion 104 of implant 100A as shown in FIG. 43.

Figure 44:
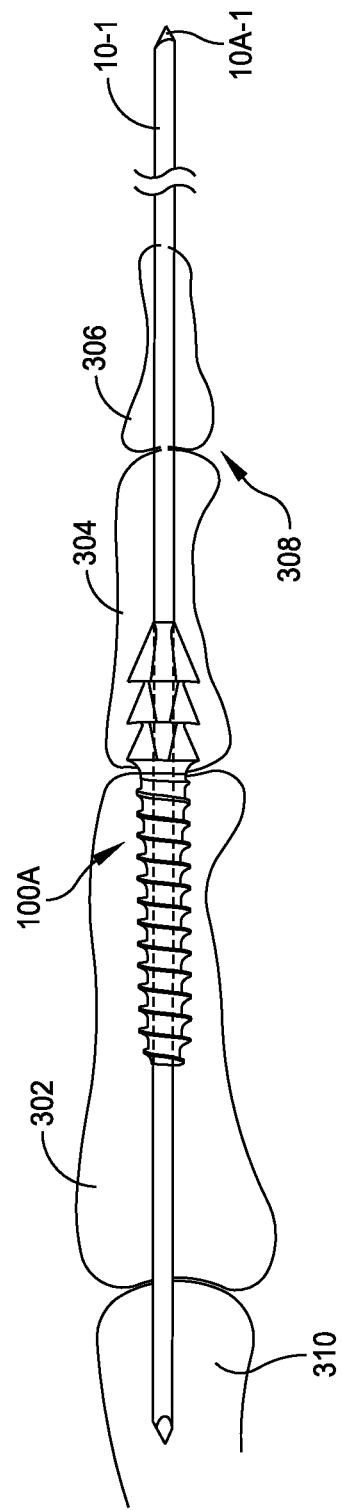
FIG. 44 illustrates the first surgical device being advanced into the proximal phalange and metatarsal in accordance with some embodiments.

At optional block 2016 (FIG. 37), end 10B-1 of k-wire 10-1 is advanced through proximal phalange 302, and into metatarsal 310 (and/or cuneiform (not shown)) as shown in FIG. 44.

Figure 45:
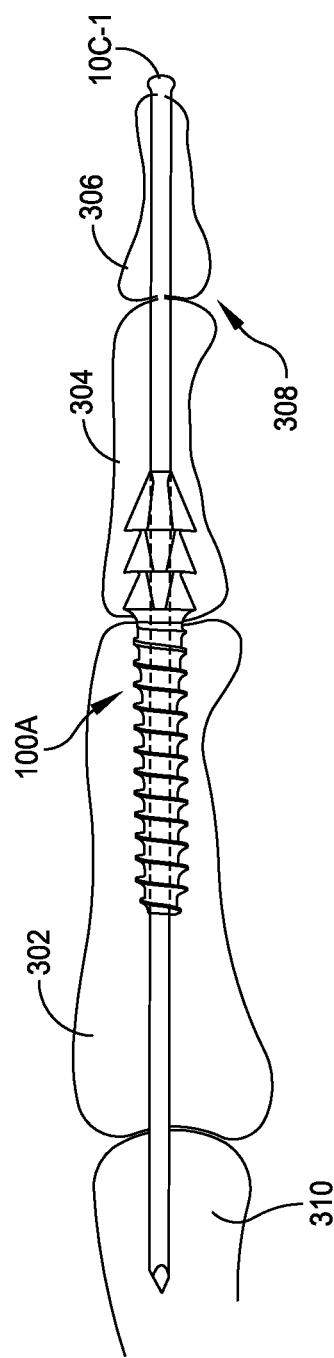
FIG. 45 illustrates one example of an end of the first surgical device having a blunted end while disposed within the middle, proximal, and distal phalanges and within the implant in accordance with some embodiments.

At optional block 2018 (FIG. 37), what was initially leading end 10A-1 (FIGS. 40, 41, 42A, and 42B), is blunted or capped to provide an exposed blunt end 10C-1 as shown in FIG. 45.

Figure 46:
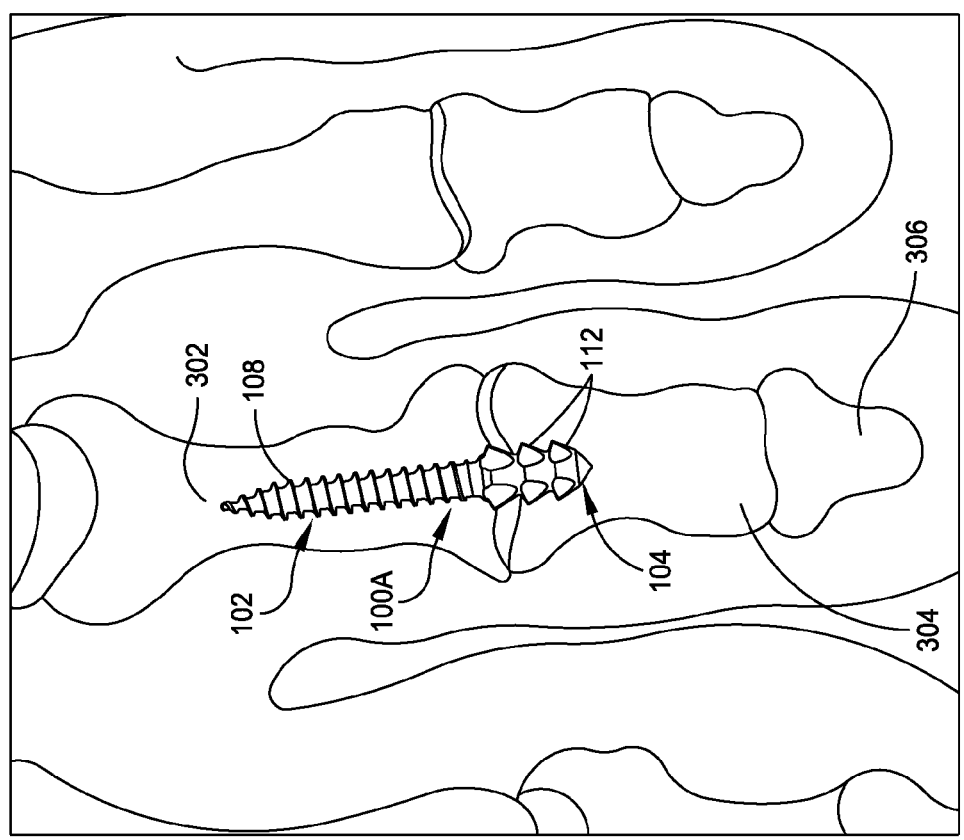
FIG. 46 illustrates a hammer toe implant installed in the middle and proximal phalanges in accordance with some embodiments.

At block 2020, after the surgical device 10-1 remains within a patient for a period of time, e.g., minutes, hours, days, or months, the surgical device 10-1 is removed to leave behind implant 100A as shown in FIG. 46.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

Some embodiments provide an implant including an elongated threaded portion and a blade portion extending from the elongated threaded portion. The blade portion has a substantially cylindrical cross-sectional geometry and a taper defined by a plurality of blades.

Some embodiments provide an implant including an elongated threaded portion and a blade portion extending from the elongated threaded portion. The blade portion includes a plurality of blades having respective substantially cruciform cross-sectional geometries defined by a grooved portion being disposed in each quadrant of each blade.

Some embodiments provide a method including forming an incision to gain access to a joint between first and second bones, flexing the first and second bones such that the bones are disposed at an angle from one another, and advancing a threaded portion of an implant into the first bone. The implant includes a blade portion extending from an elongated threaded portion. The blade portion has a substantially cylindrical cross-sectional geometry and a taper defined by a plurality of blades. The method also includes repositioning the second bone such that a middle of the second bone is approximately aligned with the blade portion of the implant and forcing the second bone into engagement with the blade portion of the implant.

Although the invention has been described in terms of exemplary embodiments, it is not limited thereto. Rather, the appended claims should be construed broadly, to include other variants and embodiments of the invention, which can be made by those skilled in the art without departing from the scope and range of equivalents of the invention.

What is claimed is:

1. A method, comprising:
   inserting a first surgical device into an exposed first end of a first bone until a trailing end of the first surgical device is disposed adjacent to the first end of the first bone;
   inserting a second surgical device into an exposed first end of a second bone while the first surgical device remains disposed within the first bone;
   advancing a first portion of an implant into the second bone while being engaged with a passageway defined by the implant such that the implant is guided by the second surgical device;
   removing the second surgical device from the second bone and from its engagement with the implant;
   repositioning the first bone such that the first surgical device is aligned with the passageway defined by the implant; and
   forcing the first bone into engagement with a second portion of the implant.

2. The method of claim 1, further comprising
   forming an incision to gain access to a joint between the first bone and the second bone;
   flexing the first bone relative to the second bone to expose the first end of the first bone and the first end of the second bone; and
   resecting at least one of the first end of the first bone and the first end of the second bone.

3. The method of claim 1, further comprising removing the first surgical device from the first bone and its engagement with the implant.

4. The method of claim 1, wherein the passageway is a central passageway that extends through the entirety of the implant.

5. The method of claim 1, wherein the first portion of the implant is a threaded portion and the second portion of the implant is a blade portion.

6. A method, comprising:
   forming an incision to gain access to a joint between first and second bones;
   flexing the first and second bones such that the first and second bones are disposed at an angle with respect to one another;
   inserting a first surgical device into the first bone until a first end of the first surgical device is disposed adjacent to a first end of the first bone;
   inserting a second surgical device into the second bone while the first surgical device remains disposed within the first bone;
   advancing a first portion of an implant into the second bone while a passageway defined by the implant is engaged with the second surgical device such that the implant is guided by the second surgical device;
   removing the second surgical device from the second bone and from its engagement with the implant;
   repositioning the first bone such that the first surgical device is aligned with the passageway defined by the implant; and
   forcing the first bone into engagement with a second portion of the implant.

7. The method of claim 6, further comprising removing the first surgical device from the first bone and its engagement with the implant.

8. The method of claim 6, further comprising resecting an end of each the first and second bones prior to inserting the first and second surgical devices.

9. The method of claim 6, wherein the first bone is a middle phalange of a foot, and the second bone is a proximal phalange of the foot.

10. The method of claim 9, wherein the first portion of the implant is a threaded portion and the second portion of the implant is a blade portion.

11. A surgical method, comprising:
    gaining access to a joint between a middle phalange and a proximal phalange;
    inserting a first end of a first surgical device into a proximal end of the middle phalange;
    advancing the first surgical device into the middle phalange and a distal phalange until a second end of the first surgical device is disposed adjacent to the proximal end of the middle phalange;
    inserting a first end of a second surgical device into a distal end of the proximal phalange while the first surgical device remains disposed within the middle and distal phalanges;
    advancing a first portion of an implant into the proximal phalange using the second surgical device as a guide;
    removing the second surgical device;
    inserting the first surgical device into a passageway defined by the implant while the first surgical device remains disposed within the middle and distal phalange; and
    removing the first surgical device from its engagement with the implant, middle phalange, and distal phalange.

12. The surgical method of claim 11, further comprising:
    advancing a second end of the first surgical device through the proximal phalange and into at least one of a metatarsal and a cuneiform; and
    blunting the first end of the first surgical device.

13. The surgical method of claim 12, further comprising, after a period of time, removing the first surgical device while the implant remains engaged with the proximal phalange and the middle phalange.

14. The surgical method of claim 11, further comprising resecting an end of each the middle phalange and the proximal phalange prior to inserting the first and second surgical devices.

15. The surgical method of claim 11, wherein the passageway is a central passageway that extends through the entirety of the implant.

16. The surgical method of claim 11, wherein the first portion of the implant is a threaded portion and the second portion of the implant is a blade portion.

* * * * *